(12) United States Patent
Xiang et al.

(10) Patent No.: US 8,193,242 B2
(45) Date of Patent: *Jun. 5, 2012

(54) LEVODOPA PRODRUG MESYLATE, COMPOSITIONS THEREOF, AND USES THEREOF

(75) Inventors: Jia-Ning Xiang, Palo Alto, CA (US); Xuedong Dai, San Jose, CA (US); Cindy X. Zhou, Palo Alto, CA (US); Jianhua Li, Sunnyvale, CA (US); Mark Q. Nguyen, San Jose, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/010,419

(22) Filed: Jan. 20, 2011

(65) Prior Publication Data

US 2011/0111062 A1     May 12, 2011

Related U.S. Application Data

(60) Continuation of application No. 12/489,146, filed on Jun. 22, 2009, now Pat. No. 7,893,105, which is a division of application No. 11/634,354, filed on Dec. 4, 2006, now Pat. No. 7,563,821.

(60) Provisional application No. 60/741,876, filed on Dec. 5, 2005.

(51) Int. Cl.
*A61K 31/24* (2006.01)
*A61P 25/00* (2006.01)

(52) U.S. Cl. ......... 514/517; 514/533; 514/534; 514/537

(58) Field of Classification Search ........................ None
See application file for complete search history.

(56) References Cited

U.S. PATENT DOCUMENTS

| | | | |
|---|---|---|---|
| 3,811,444 A | 5/1974 | Heller et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien et al. |
| 4,038,411 A | 7/1977 | Saari |
| 4,066,747 A | 1/1978 | Capozza |
| 4,070,347 A | 1/1978 | Schmitt |
| 4,079,038 A | 3/1978 | Choi et al. |
| 4,083,949 A | 4/1978 | Benedikt |
| 4,093,709 A | 6/1978 | Choi et al. |
| 4,134,991 A | 1/1979 | Wermuth |
| 4,180,509 A | 12/1979 | Metcalf et al. |
| 4,311,706 A | 1/1982 | Bodor et al. |
| 4,663,349 A | 5/1987 | Repta |
| 4,771,073 A | 9/1988 | Repta |
| 4,826,875 A | 5/1989 | Chiesi |
| 4,873,263 A | 10/1989 | Repta |
| 4,914,222 A | 4/1990 | Budavari et al. |
| 4,966,915 A | 10/1990 | Tsuchiya et al. |
| 4,983,400 A | 1/1991 | Dempski et al. |
| 5,017,607 A | 5/1991 | Chiesi |
| 5,057,321 A | 10/1991 | Edgren et al. |
| 5,073,641 A | 12/1991 | Bundgaard et al. |
| 5,128,145 A | 7/1992 | Edgren et al. |
| 5,133,974 A | 7/1992 | Paradissis et al. |
| 5,190,763 A | 3/1993 | Edgren et al. |
| 5,283,352 A | 2/1994 | Backstrom et al. |
| 5,332,576 A | 7/1994 | Mantelle |
| 5,462,933 A | 10/1995 | Kramer et al. |
| 5,607,969 A | 3/1997 | Milman et al. |
| 5,698,155 A | 12/1997 | Grosswald et al. |
| 5,827,819 A | 10/1998 | Yatvin et al. |
| 5,840,756 A | 11/1998 | Cohen et al. |
| 6,696,600 B2 | 2/2004 | Frenkel et al. |
| 7,101,912 B2 | 9/2006 | Xiang et al. |
| 7,323,585 B2 | 1/2008 | Xiang et al. |
| 7,342,131 B2 | 3/2008 | Xiang et al. |
| 7,534,813 B2 | 5/2009 | Xiang et al. |
| 7,563,821 B2 | 7/2009 | Xiang et al. |
| 7,671,089 B2 | 3/2010 | Xiang et al. |
| 7,709,527 B2 | 5/2010 | Xiang et al. |
| 7,893,105 B2 | 2/2011 | Xiang et al. |
| 7,956,212 B2 | 6/2011 | Xiang et al. |
| 7,968,597 B2 | 6/2011 | Xiang et al. |
| 2002/0099041 A1 | 7/2002 | Gallop et al. |
| 2003/0152628 A1 | 8/2003 | Licht et al. |
| 2003/0158254 A1 | 8/2003 | Zerangue et al. |
| 2005/0209181 A1 | 9/2005 | Akil et al. |
| 2005/0282891 A1 | 12/2005 | Xiang et al. |
| 2006/0020028 A1 | 1/2006 | Xiang et al. |
| 2007/0225366 A1 | 9/2007 | Xiang et al. |
| 2008/0070984 A1 | 3/2008 | Tran |

(Continued)

FOREIGN PATENT DOCUMENTS

CA     2607198     11/2006

(Continued)

OTHER PUBLICATIONS

Airaksinen et al., Excipient selection can significantly affect sold-state phase transformation in formulation during we granulation. *AAPS PharmSciTech* 2005, 6(2), E311-E322.

(Continued)

*Primary Examiner* — Rosalynd Keys

(74) *Attorney, Agent, or Firm* — Kilpatrick Townsend & Stockton LLP

(57) ABSTRACT

(2R)-2-Phenylcarbonyloxypropyl (2S)-2-amino-3-(3,4-dihydroxyphenyl)propanoate mesylate and crystalline form thereof, methods of making the same, pharmaceutical compositions thereof, and methods of using the same to treat diseases or disorders such as Parkinson's disease are provided.

14 Claims, 6 Drawing Sheets

U.S. PATENT DOCUMENTS

| | | | |
|---|---|---|---|
| 2008/0103200 A1 | 5/2008 | Xiang et al. | |
| 2008/0132570 A1 | 6/2008 | Xiang et al. | |
| 2008/0171789 A1 | 7/2008 | Xiang et al. | |
| 2008/0214663 A1 | 9/2008 | Mantelle | |
| 2009/0137834 A1 | 5/2009 | Xiang et al. | |
| 2009/0156679 A1 | 6/2009 | Xiang et al. | |
| 2010/0099761 A1 | 4/2010 | Karaborni et al. | |
| 2010/0099907 A1 | 4/2010 | Raillard et al. | |
| 2010/0173992 A1 | 7/2010 | Xiang et al. | |
| 2011/0028544 A1 | 2/2011 | Xiang et al. | |
| 2011/0111024 A1 | 5/2011 | Mao et al. | |
| 2011/0111062 A1 | 5/2011 | Xiang et al. | |
| 2011/0201817 A1 | 8/2011 | Xiang et al. | |

FOREIGN PATENT DOCUMENTS

| | | |
|---|---|---|
| EP | 0 309 827 B1 | 4/1989 |
| GB | 1447599 | 8/1976 |
| GB | 1537951 | 1/1979 |
| JP | 58-024547 | 2/1983 |
| WO | WO 86/04579 | 8/1986 |
| WO | WO 88/01615 A1 | 3/1988 |
| WO | WO 01/68065 A2 | 9/2001 |
| WO | WO 02/28882 A1 | 4/2002 |
| WO | WO 2007/087256 A2 | 8/2007 |

OTHER PUBLICATIONS

Alpert and Friedhoff, Paradoxical reaction to L-dopa in schizophrenic patients. *Am J Psychiatry* 1978, 135(11), 1329-1332.

Bai, pGlu-L-Dopa-Pro: A tripeptide prodrug targeting the intestinal peptide transporter for absorption and tissue enzymes for conversion. *Pharm. Res.* 1995, 12(7), 1101-1104.

Berge et al., Pharmaceutical salts. *J. Pharm. Sci.* 1977, 66(1), 1-19.

Betarbet et al., Animal models of Parkinson's disease. *Bioessays* 2002, 24(4), 308-18.

Bodor et al., Improved delivery through biological membranes. 4. Prodrugs of L-Dopa. *J. Med. Chem.* 1977, 20(11), 1435-1445.

Boivin and Montplaisir, The effects of L-dopa on excessive daytime sleepiness in narcolepsy. *Neurology* 1991, 41, 1267-1269.

Bonelli and Wenning, Pharmacological management of Huntington's disease: an evidence-based review. *Current Pharmaceutical Design* 2006, 12(21), 2701-2720.

Bruno and Bruno, Effects of L-dopa on pharmacological parkinsonism. *Acta Psychiatr Scand* 1966, 4(3), 264-271.

Buchanan et al., Double blind trial of L-dopa in chronic schizophrenia. *Aust N Z J Psychiatry* 1975, 9(4), 269-271.

Carboxylic Acid Derivatives and Nitriles, http://www.chem.uky.edu/Courses/che232/JEA/In/9.%20Esters_etc.pdf, retrieved Mar. 24, 2010.

Cho et al., Dopamine neurons derived from embryonic stem cells efficiently induce behavioral recovery in a Parkinsonian rat model. *Biochem. Biophys. Res. Commun* 2006, 341(1), 6-12.

Coleman et al., A practical guide to polymer miscibility. *Polymer* 1990, 31, 1187-1203.

Conti et al., Levodopa for idiopathic restless legs syndrome: evidence-based review, *Mot Disord* 2007, 22(13), 1943-1951.

Cools, Dopaminergic modulation of cognitive function-implications for L-dopa treatment in Parkinson's disease. *Neuroscience Biobehavioral Rev* 2006, 30, 1-23.

Cooper et al., L-Dopa esters as potential prodrugs: behavioural activity in experimental models of Parkinson's disease. *J. Pharm. Pharmacol.* 1987, 39, 627-635.

Davey et al., Polymorphism in molecular crystals: stabilization of a metastable form by conformational mimicry. *J Am Chem Soc* 1997, 119(7), 1767-1772.

Di Stefano et al., Dimeric L-Dopa derivatives as potential prodrugs. *Bioorganic & Medicinal Chem. Lett.* 2001, 11, 1085-1088.

Doggrell, The therapeutic potential of dopamine modulators on the cardiovascular and renal systems. *Expert Opin. Investig. Drugs*, 2002, 11(5), 631-644.

Durif et al., Worsening of levodopa-induced dyskinesias by motor and mental tasks. *Mov Disord* 1999, 14, 242-245.

During et al., Controlled release of dopamine from a polymeric brain implant: In vivo Characterization. *Ann. Neurol.* 1989, 25(4), 351-356.

Ebadi and Srinivasan, Pathogenesis, prevention and treatment of neuroleptic-induced movement disorders. *Pharmacological Reviews* 1995, 47(4), 575-604.

Eltayb et al., Enhanced cortical dopamine output and antipsychotic-like effect of raclopride with adjunctive low-dose L-dopa. *Biol Psychiatry* 2005, 58, 337-343.

Emborg, Evaluation of animal models of Parkinson's disease for neuroprotective strategies. *J. Neurosci Methods* 2004, 139(2), 121-143.

Fahn et al., Levodopa and the progression of Parkinson's disease. *N. Engl J Med* 2004, 351(24), 2498-2508.

Faulkner et al, *Ann. Pharmacother.* 2003, 37(2), 282-6.

Fincher, Particle size of drugs and its relationship to absorption and activity. *J. Pharm. Sci.* 1968, 57(11), 1825-1835.

Fix et al., Short-chain alkyl esters of L-Dopa as prodrugs for rectal absorption. *Pharm. Res.*1989, 6(6), 501-505.

Fix et al., A comparison of oral and rectal absorption of L-Dopa esters in rats and mice. *Pharm. Res.* 1990, 7(4), 384-387.

Floel et al., Dopaminergic effects on encoding of a motor memory in chronic stroke. *Neurology* 2005, 65(3), 472-474.

Floel et al., Levodopa increases memory encoding and dopamine release in the striatum in the elderly. *Neurobiology of Aging* 2008PMID 17098331.

Folstein et al., Mini-mental state. A practical method for grading the cognitive state of patients for the clinician. *J Psychiatr Res* 1975, 12(3), 189-198.

Garcia-Borreguero et al., Treatment of restless legs syndrome with gabapentin: a double-blind, cross-over study, *Neurol.* 2002, 1573-79, vol. 59, No. 10.

Garzon-Aburbeh et al., A lymphotropic prodrug of L-Dopa: synthesis, pharmacological properties, and pharmacokinetic behavior of 1,3-dihexadecanoyl-2-[($S$)-2-amino-3-(3,4-dihydroxyphenyl)propanoyl]propane-1,2,3-triol. *J. Med. Chem.* 1986, 29, 687-691.

Gelb et al., Diagnostic criteria for Parkinson disease. *Arch Neurol* 1999, 56(1), 33-9.

Gerlach and Luhdorf, The effect of L-dopa on young patients with simple schizophrenia, treated with neuroleptic drugs. *Psychopharmacologia* 1975, 44(1), 105-110.

Gibb and Lees, The relevance of the Lewy body to the pathogenesis of idiopathic Parkinson's disease. *J Neurol Neurosurg Psychiatry* 1988, 51(6), 745-752.

Giovannoni et al., Bradykinesia akinesia inco-ordination test (BRAIN TEST): an objective computerized assessment of upper limb motor function. *J Neurol Neurosurg Psychiatry* 1999, 67, 624-629.

"Guidance for Industry—Bioavailability and Bioequivalence Studies for Orally Administered Drug Products—General Considerations," U.S. Department of Health and Human Services, FDA-CDER, Mar. 2003, pp. 1-26.

Hirsch et al., Animal models of Parkinson's disease in rodents induced by toxins: an update. *J Neural Transm Suppl* 2003, 65, 89-100.

Hisaka et al., Absorption of a novel prodrug of L-Dopa, L-3-(3-hydroxy-4-pivaloyloxyphenyl)alanine (NB-355). *In Vitro and In Situ Studies, Drug Metabolism and Disposition* 1990, 18(5), 621-625.

Hogl et al., Increased daytime sleepiness in Parkinson's disease: a questionnaire survey. *Movement Disorders* 2003, 18(3), 319-323.

Howard et al., Intracerebral drug delivery in rats with lesion-induced memory deficits. *J. Neurosurg* 1989, 71, 105-112.

Inanaga et al., Double-blind controlled study of L-dopa therapy in schizophrenia. *Folia Psychiatr Neurol Jpn* 1975, 29(2), 123-143.

Ishikura et al., Database CAS citation 1994:701312 [retrieved Nov. 23, 2009] from STN; Columbus, OH USA.

Ishikura et al., Database CAS citation 1995:365090 [retrieved Nov. 23, 2009] from STN; Columbus, OH USA.

Ishikura et al., Drug delivery to the brain. DOPA prodrugs based on a ring-closure reaction to quaternary thiazolium compounds. *Int'l. J. Pharmaceutics* 1995, 116, 51-63.

Jankovic, Treatment of dystonia. *Lancet Neurol* 2006, 5(10), 864-872.

Jaskiw and Popli, A meta-analysis of the response to chronic L-dopa in patients with schizophrenia: therapeutic and heuristic implications. *Psychopharmacology* 2004, 171, 365-374.

Juncos et al., Levodopa methyl ester treatment of Parkinson's disease. *Neurology* 1987, 37, 1242-1245.

Kay and Opler, L-dopa in the treatment of negative schizophrenic symptoms: a single-subject experimental study. *Int'l J Psychiatry Med* 1985-86, 15(3), 293-298.

Knecht et al., Levodopa: faster and better word learning in normal humans. *Ann. Neurol* 2004, 56(1), 20-26, July.

Kulisevsky, Role of dopamine in learning and memory: implications for the treatment of cognitive dysfunction in patients with Parkinson's disease. *Drugs Aging* 2000, 16(5), 365-379.

Langer, New methods of drug delivery. *Science* 1990, 249, 1527-1533.

Langer and Peppas, Chemical and physical structure of polymers as carriers for controlled release of bioactive agents: a review. *JMS-Rev. Macromol. Chem. Phys.* 1983, C23(1), 61-126.

Leong and Langer, Polymeric controlled drug delivery. *Advanced Drug Delivery Reviews* 1987, 1, 199-233.

Leppert et al., .The effects of carbidopa dose and time and route of administration on systemic L-Dopa levels in rats. *Pharmaceutical Res* 1988, 5(9), 587-591.

Levy et al, Inhibition of calcification of bioprosthetic heart valves by local controlled-release diphosphonate. *Science* 1985, 228, 190-192.

Lu and Yu, Dimensionless presentation for drug release from a coated pure drug bead: 2. Experiment. *Int. J. Pharmaceutics* 1994, 112, 117-124.

Ludatsher, Stable remission of tardive dyskinesia by L-dopa. *J Clin Psychopharm* 1989, 9(1), 39-41.

Manson et al., An ambulatory dyskinesia monitor. *J Neurol Neurosurg Psychiatry* 2000, 68(2), 196-201.

Marrel et al., L-Dopa esters as potential prodrugs. *Eur. J. Med. Chem. Chim. Ther.* 1985, 5, 459-465.

Movement Disorder Society Task Force, The Unified Parkinson's Disease Rating Scale (UPDRS): status and recommendations. *Mov Disord* 2003, 18(7), 738-50.

NUTT Response to levodopa treatment in dopa-responsive dystonia. *Arch Neurol* 2001, 58, 905-910.

Olanow et al., Drug insight: continuous dopaminergic stimulation in the treatment of Parkinson's disease. *Nat Clin Pract Neurol* 2006, 2(7), 382-92, July.

Olson et al., Gabapentin for parkinsonism: a double-blind, placebo-controlled, crossover trial. *Am. J. Med.* 1997, 102(1), 60-6.

Ondo and Jankovic, Restless legs syndrome: clinicoetiologic correlates. *Neurology* 1996, 47(6), 1435-1441.

O'Neill et al., LY503430: pharmacology, pharmacokinetics, and effects in rodent models of Parkinson's disease. *CNS Drug Rev.* 2005, 11(1), 77-96.

Orth and Tabrizi, Models of Parkinson's disease. *Mov Disord* 2003, 18(7), 729-37.

O'Suilleabhain and Dewey, Contributions of dopaminergic drugs and disease severity to daytime sleepiness in Parkinson disease. *Arch. Neurol* 2002, 59, 986-989.

Paus et al., Sleep attacks, daytime sleepiness, and dopamine agonists in Parkinson's disease. *Movement Disorders* 2003, 18(6), 659-667.

Racette and Perlmutter, Levodopa responsive parkinsonism in an adult with Huntington's disease. *J Neurol Neurosurg Psychiatry* 1998, 65(4), 577-579.

Rascol and Fabre, Dyskinesia: L-Dopa-induced and tardive dyskinesia. *Clinical Neuropharmacology* 2001, 24(6), 313-323.

Rouhi, The Right Stuff. *Science and Technology*, C&E News Feb. 2003, 32-35.

Saari, abstract, Database CAS citation 1978:444225 [retrieved Mar. 24, 2010] from STN; Columbus, OH, USA.

Sasahara et al., Dosage form design for improvement of bioavailability of levodopa II: bioavailability of marketed levodopa preparations in dogs and Parkinsonian patients. *J. Pharm. Sci.* 1980, 69(3), 261-265.

Saudek et al., A preliminary trial of the programmable implantable medication system for insulin delivery. *N. Engl. J. Med.* 1989, 321, 574-579.

Scheidtmann et al., Effect of levodopa in combination with physiotherapy on functional motor recovery after stroke: a prospective, randomized, double-blind study. *Lancet* 2001, 358(9284), 787-790.

Schneider et al., Familial dopa-responsive cervical dystonia, *Neurology* 2006, 66(4), 599-601.

Sefton, Implantable pumps. *CRC Critical Reviews in Biomedical Engineering* 1987, 14(3), 201-240.

Silber, Sleep disorders. *Neurologic Clin* 2001, 19(1), 173-186.

Soares and McGrath, The treatment of tardive dyskinesia—a systematic review and meta-analysis. *Schizophrenia Research* 1999, 39, 1-16.

Staab et al., Control of polymorphism by 'tailor-mad' polymeric crystallization auxiliaries. Preferential precipitation of a metastable polar form for second harmonic generation. *Adv Mater* 1990, 2(1), 40-43.

Tang et al., Synthesis and characterization of water-soluble and photostable L-dopa dendrimers. *Organic Letters* 2006, 8(20), 4421-4424.

Tolwani et al., Experimental models of Parkinson's disease: insights from many models. *Lab Anim Sci* 1999, 49(4), 363-71.

Van Blercom et al., Effects of gabapentin on the motor response to levodopa: a double-blind, placebo-controlled, crossover study in patients with complicated Parkinson disease. *Clin Neuropharmacol* 2004, 27(3), 124-8.

Verma et al., Osmotically controlled oral drug delivery. *Drug Development and Industrial Pharmacy* 2000, 26(7), 695-708.

Von Scheele, Levodopa in restless legs. *Lancet* 1986, 2(8504), 426-427.

Wang et al., Preparation and intestinal absorption of L-Dopa-D-phenylglycine. *J. Food and Drug Analysis* 2002, 10(2), 81-87.

Wang et al., Synthesis and pharmacological activities of a novel tripeptide mimetic dopamine prodrug. *Bioorganic & Medicinal Chemistry Letters* 1995, 5(19), 2195-2198.

Wikstrom et al., Manipulating theophylline monohydrate formation during high-shear wet granulation through improved understanding of the role of pharmaceutical excipients. *Pharmaceutical Research* 2008, 25(4), 923-935, April.

International Search Report and Written Opinion mailed Nov. 3, 2005, for International Application No. PCT/US2005/019492, filed Jun. 3, 2005.

International Search Report and Written Opinion mailed Nov. 3, 2005, for International Application No. PCT/US2005/019493, filed Jun. 3, 2005.

International Search Report and Written Opinion mailed Jul. 23, 2007, for International Application No. PCT/US2006/046273, filed Dec. 4, 2006.

International Search Report and Written Opinion of the International Searching Authority mailed Apr. 15, 2008, for International Application No. PCT/US2007/026200 filed Dec. 20, 2007.

International Search Report and Written Opinion of the International Searching Authority mailed May 14, 2008, for International Application No. PCT/US2007/026271, filed Dec. 20, 2007.

International Search Report and Written Opinion of the International Searching Authority mailed May 27, 2008, for International Application No. PCT/US2007/078541, filed Sep. 14, 2007.

Office Action mailed Nov. 24, 2006, for U.S. Appl. No. 11/145,159, filed Jun. 3, 2005.

Final Office Action mailed Jun. 15, 2007, for U.S. Appl. No. 11/145,159, filed Jun. 3, 2005.

Office Action mailed Jan. 19, 2007, for U.S. Appl. No. 11/145,280, filed Jun. 3, 2005.

Office Action mailed Apr. 17, 2007, for U.S. Appl. No. 11/145,280, filed Jun. 3, 2005.

Office Action mailed Oct. 24, 2008, for U.S. Appl. No. 12/001,618, filed Dec. 11, 2007.

Office Action mailed Jun. 3, 2008, for U.S. Appl. No. 12/008,473, filed Jan. 10, 2008.

Office Action mailed Mar. 21, 2008, for U.S. Appl. No. 11/634,354, filed Dec. 4, 2006.

Office Action mailed Sep. 16, 2008, for U.S. Appl. No. 11/634,354, filed Dec. 4, 2006.
Office Action mailed Aug. 7, 2009, for U.S. Appl. No. 12/005,117, filed Dec. 20, 2007.
Office Action mailed Dec. 1, 2009, (later vacated) for U.S. Appl. No. 12/364,453, filed Feb. 2, 2009.
Office Action mailed Apr. 1, 2010, for U.S. Appl. No. 12/364,453, filed Feb. 2, 2009.
Office Action mailed Aug. 30, 2010, for U.S. Appl. No. 12/364,453, filed Feb. 2, 2009.
Office Action mailed Jan. 25, 2010, for U.S. Appl. No. 12/005,120, filed Dec. 20, 2007.
Office Action mailed May 4, 2010, for U.S. Appl. No. 12/347,807, filed Dec. 31, 2008.
Office Action mailed Oct. 18, 2010, for U.S. Appl. No. 12/347,807, filed Dec. 31, 2008.
Office Action mailed Apr. 28, 2010, for U.S. Appl. No. 12/489,146, filed Jun. 22, 2009.
Notice of Allowance mailed Jun. 25, 2010, for U.S. Appl. No. 12/005,120, filed Dec. 20, 2007.
Notice of Allowance mailed Dec. 16, 2009, for U.S. Appl. No. 12/005,117, filed Dec. 20, 2007.
Notice of Allowance mailed Jun. 22, 2009, for U.S. Appl. No. 11/634,354, filed Dec. 4, 2006.
Notice of Allowance mailed Oct. 15, 2008, for U.S. Appl. No. 12/008,473, filed Jan. 10, 2008.
Notice of Allowance mailed May 29, 2009, for U.S. Appl. No. 12/001,618, filed Dec. 11, 2007.
Notice of Allowance, Notice of Allowability, and Examiner's Amendment mailed Sep. 11, 2007, for U.S. Appl. No. 11/145,280, filed Jun. 3, 2005.
Notice of Allowance mailed Oct. 10, 2007, for U.S. Appl. No. 11/145,159, filed Jun. 3, 2005.
Notice of Allowance mailed Jan. 23, 2008, for U.S. Appl. No. 11/145,159, filed Jun. 3, 2005 (Supplemental).
Notice of Allowance mailed Oct. 12, 2010, for U.S. Appl. No. 12/489,146, filed Jun. 22, 2009.
Notice of Allowance mailed Mar. 20, 2009, for U.S. Appl. No. 11/634,354, filed Dec. 4, 2006.
Notice of Allowance mailed Jan. 6, 2011, for U.S. Appl. No. 12/364,453.
U.S. Appl. No. 12/726,978, filed Mar. 18, 2010.
Notice of Allowance mailed Feb. 17, 2011 for U.S. Appl. No. 12/347,807, filed Dec. 31, 2008.
Office Action, mailed on Sep. 22, 2011 for U.S. Appl. No. 13/095,101, filed Apr. 27, 2011.
U.S. Appl. No. 13/095,101, filed Apr. 27, 2001, Xiang et al.

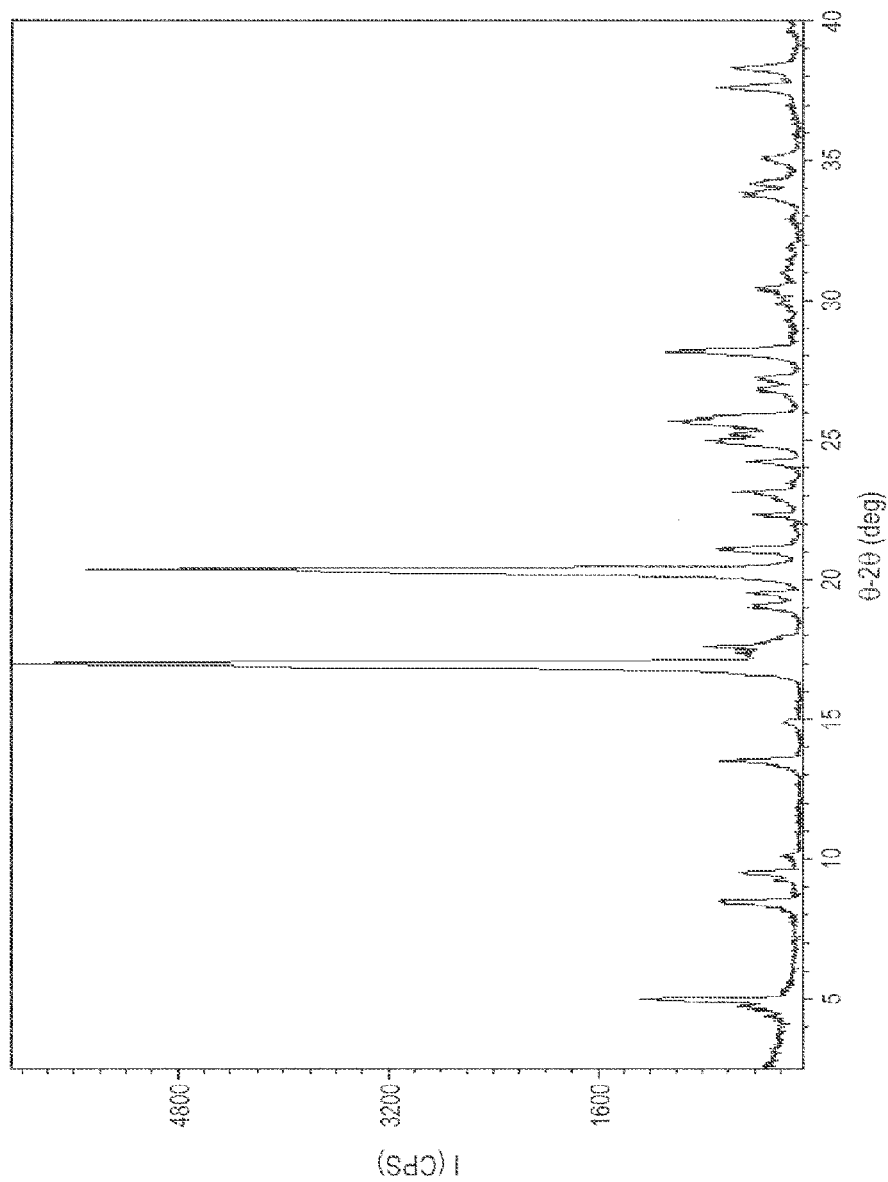

LEVODOPA PRODRUG MESYLATE, COMPOSITIONS THEREOF, AND USES THEREOF

This application is a continuation of U.S. patent application Ser. No. 12/489,146 filed on Jun. 22, 2009, now U.S. Pat. No. 7,893,105, which is a divisional of U.S. patent application Ser. No. 11/634,354 filed on Dec. 4, 2006, now U.S. Pat. No. 7,563,821, which claims benefit of U.S. Provisional Patent Application No. 60/741,876 filed on Dec. 5, 2005, each of which is incorporated by reference herein for all purposes.

Disclosed herein is a mesylate salt of a levodopa prodrug and a crystalline form thereof, and pharmaceutical compositions containing the same, useful for treating diseases or disorders such as Parkinson's disease.

Parkinson's disease is a disabling, progressive illness that affects one in 1,000 people and generally occurs in people over the age of 50 years. Patients with Parkinson's disease have a deficiency of the neurotransmitter dopamine in the brain as a result of nigrostriatal pathway disruption caused by degeneration of the substantia nigra. Levodopa (L-dopa or L-3,4-dihydroxyphenylalanine), an immediate precursor of dopamine, is the most commonly prescribed drug for treatment of this disease.

Following oral administration, levodopa is rapidly absorbed via an amino acid transporter present in the upper small intestine. Due to the narrow distribution of this transporter system, the window available for levodopa absorption is limited and the extent of absorption can depend on the rate at which the drug passes through the upper gastrointestinal tract.

Intestinal metabolism of levodopa is the major source of first pass loss of the drug. Approximately 35% of an administered dose of levodopa reaches the systemic circulation as intact levodopa after oral administration in patients (Sasahara, *J. Pharm. Sci* 1990, 69, 261). Once absorbed, levodopa is rapidly metabolized to dopamine by L-aromatic amino acid decarboxylase (AADC) enzymes in the peripheral tissues (e.g., intestines and liver). For this reason, levodopa is normally co-administered with a decarboxylase enzyme inhibitor such as carbidopa or benserazide. When administered with carbidopa, the plasma concentration of intact levodopa increases and thus more levodopa becomes available to be transported into the central nervous system where it is converted to dopamine. Carbidopa and benserazide do not cross the blood-brain barrier to a significant extent and therefore do not inhibit the required conversion of levodopa to dopamine in the brain.

The use of prodrugs of levodopa to improve the pharmacokinetics of levodopa has been proposed. Many of these prodrugs are simple esters of levodopa (see U.S. Pat. Nos. 5,017,607; 4,826,875; 4,873,263; 4,771,073; 4,663,349; 4,311,706; Japanese Patent No. JP58024547; Juncos et al., *Neurology* 1987, 37, 1242; and Cooper et al., *J. Pharm. Pharmacol.* 1987, 39, 627-635). An oral formulation of levodopa methyl ester (Levomet®, CHF 1301) has been described (Chiesi Pharmaceuticals). The ethyl ester of levodopa (TV-1203) is under clinical investigation as a potential therapy for Parkinson's disease when co-administered with carbidopa (U.S. Pat. No. 5,607,969, which is incorporated herein by reference in its entirety). A sustained release cellulose formulation of levodopa ethyl ester in a mixture of hydroxypropylmethyl cellulose, hydroxypropyl cellulose, and a carboxyvinyl polymer has also been described (U.S. Pat. No. 5,840,756). However, oral administration of this formulation to healthy adults pretreated with carbidopa produced a plasma levodopa terminal half-life of only 2 hours, comparable to that of Sinemet® CR.

A pivaloyl ester of levodopa (NB-355) has been described (European Patent No. 0 309 827). Following oral administration of NB-355, a rapid increase in the plasma concentration or in the elimination of levodopa was not observed and the duration of circulating levodopa was prolonged, although plasma concentrations of levodopa were low. The potential for using ester prodrugs of levodopa to enhance rectal absorption of the drug has also been described (U.S. Pat. Nos. 4,663,349; 4,771,073; and 4,873,263). Notably, the absorption of simple alkyl esters of levodopa has been shown to be greater following rectal absorption than following oral dosing (Fix, et al., *Pharm. Res.* 1989, 6, 501-5; and Fix, et al., *Pharm. Res.* 1990, 4, 384-7). This effect is attributed to the decreased abundance of esterases in the large intestine relative to the small intestine. Therefore, selective delivery of a prodrug of levodopa to the large intestine in a sustained release formulation might be expected to provide a greater oral bioavailability and a prolonged systemic exposure to the drug.

A series of glycolic acid ester containing prodrugs of levodopa has been described (Wermuth, U.S. Pat. No. 4,134,991). Lipid conjugates of levodopa to facilitate the entry of levodopa into cells and tissues have also been described (Yatvin, U.S. Pat. No. 5,827,819).

Thus, the development of levodopa prodrugs that can be efficiently absorbed throughout the gastrointestinal tract, including the colon, and reduce first-pass metabolism of levodopa is highly desirable.

The human gastrointestinal tract includes the small intestine and the large intestine. The human small intestine is a convoluted tube about twenty feet in length between the stomach and large intestine. The small intestine is subdivided into the duodenum, the jejunum, and the ileum. The large intestine is about 5 feet in length and runs from the ileum to the anus. The large intestine is divided into the caecum, colon, and the rectum. The colon is divided into four parts including the ascending, traverse, descending, and the sigmoid flexure. In general, an orally ingested compound resides about 1 to 6 hours in the stomach, about 2 to 7 hours in the small intestine, and about 8 to 18 hours in the colon. Thus, the greatest period of time for sustained release of a compound occurs when the compound is passing through the colon.

Certain active transporter proteins are known to be expressed throughout the gastrointestinal tract. An active transporter refers to a membrane-bound protein that recognizes a substrate and affects the entry of the substrate into or exit from a cell by carrier-mediated transport or receptor-mediated transport. Active transport includes movement of molecules across cellular membranes that is directly or indirectly dependent on an energy mediated process, such as for example by a process driven by ATP hydrolysis, or by an ion gradient, which occurs by facilitated diffusion mediated by interaction with specific transporter proteins through a modulated solute channel. Examples of solute mediated transporters include organic cation transporters such as OCTN1 and OCTN2, which are expressed in the epithelial cells lining a human colon as well as in the small intestine.

More recently, levodopa prodrugs designed to be absorbed in both the small and large intestines have been described in Xiang et al., U.S. Application Publication Nos. 2005/0282891 and 2006/0020028, each of which is incorporated herein by reference in its entirety. These levodopa prodrugs can achieve an oral bioavailability of levodopa that is at least two times greater than the oral bioavailability of levodopa when orally administered on an equivalent molar basis. More specifically, Xiang et al., U.S. Application Publication No. 2005/0282891 discloses the compound (2R)-2-phenylcarbonyloxypropyl (2S)-2-amino-3-(3,4-dihydroxyphenyl)propanoate hydrochloride in an amorphous or crystalline form (see Example 8 of Xiang et al.). The prodrugs described by Xiang et al. can be efficaciously incorporated into sustained release formulations including osmotic delivery devices to provide sustained systemic exposure to levodopa upon oral administration to a patient.

In general, crystalline forms of drugs are preferred over amorphous forms of drugs, in part, because of their, superior stability. For example, in many situations, an amorphous drug converts to a crystalline drug form upon storage. Because amorphous and crystalline forms of a drug typically have differing physical properties, chemical properties, potencies, and/or bioavailabilities, such interconversion is undesirable for safety reasons in pharmaceutical usage. A key characteristic of any crystalline drug is the polymorphic behavior of such a material. Polymorphs are crystals of the same molecule, which have different physical properties because the crystal lattice contains a different arrangement of molecules. The different physical properties exhibited by polymorphs can affect important pharmaceutical parameters such as storage, stability, compressibility, density (important in formulation and product manufacturing), and dissolution rates (important in determining bioavailability). Stability differences may result from changes in chemical reactivity (e.g., differential hydrolysis or oxidation, such that a dosage form comprising a certain polymorph can discolor more rapidly than a dosage form comprising a different polymorph), mechanical changes (e.g., tablets can crumble on storage as a kinetically favored crystalline form converts to thermodynamically more stable crystalline form), or both (e.g., tablets of one polymorph can be more susceptible to breakdown at high humidity). Solubility differences between polymorphs may, in extreme situations, result in transitions to crystalline forms that lack potency and/or that are toxic. In addition, the physical properties of a crystalline form may also be important in pharmaceutical processing. For example, a particular crystalline form may form solvates more readily or may be more difficult to filter and wash free of impurities than other crystalline forms (i.e., particle shape and size distribution might be different between one crystalline form relative to other forms).

Agencies such as the United States Food and Drug Administration can require that the polymorphic content of a drug product be monitored and controlled if the most thermodynamically stable polymorphic form of the drug is not used and/or different polymorphic forms of the drug can affect the quality, safety, and/or efficacy of the drug product. Thus, medical and commercial reasons favor synthesizing and marketing solid drugs as a thermodynamically stable polymorph, substantially free of kinetically favored polymorphs.

Accordingly, a need exists for levodopa prodrugs and crystalline forms thereof exhibiting physicochemical properties that may be used advantageously in pharmaceutical processing and pharmaceutical compositions, and that are also sufficiently labile under physiological conditions to provide therapeutically effective plasma concentrations of levodopa, particularly when the levodopa prodrug is orally administered.

In a first aspect, the compound (2R)-2-phenylcarbonyloxypropyl (2S)-2-amino-3-(3,4-dihydroxyphenyl)propanoate mesylate is provided.

In a second aspect, crystalline (2R)-2-phenylcarbonyloxypropyl (2S)-2-amino-3-(3,4-dihydroxyphenyl)propanoate mesylate is provided.

In a third aspect, compositions comprising (2R)-2-phenylcarbonyloxypropyl (2S)-2-amino-3-(3,4-dihydroxyphenyl)propanoate mesylate and at least one other diastereomer of 2-phenylcarbonyloxypropyl-2-amino-3-(3,4-dihydroxyphenyl)propanoate mesylate wherein the diastereomeric purity of (2R)-2-phenylcarbonyloxypropyl (2S)-2-amino-3-(3,4-dihydroxyphenyl)propanoate mesylate is at least about 97% are provided.

In a fourth aspect, pharmaceutical compositions comprising at least one pharmaceutically acceptable vehicle and a therapeutically effective amount of (2R)-2-phenylcarbonyloxypropyl (2S)-2-amino-3-(3,4-dihydroxyphenyl)propanoate mesylate or crystalline form thereof are provided.

In a fifth aspect, methods of treating a disease in a patient comprising administering to a patient in need of such treatment a therapeutically effective amount of (2R)-2-phenylcarbonyloxypropyl (2S)-2-amino-3-(3,4-dihydroxyphenyl)propanoate mesylate or crystalline form thereof are provided.

In a sixth aspect, pharmaceutical compositions comprising an oral sustained release formulation of (2R)-2-phenylcarbonyloxypropyl (2S)-2-amino-3-(3,4-dihydroxyphenyl)propanoate mesylate or crystalline form thereof are provided.

In a seventh aspect, methods of preparing (2R)-2-phenylcarbonyloxypropyl (2S)-2-amino-3-(3,4-dihydroxyphenyl)propanoate mesylate comprising providing a solution of (2R)-2-phenylcarbonyloxypropyl (2S)-2-(tert-butoxycarbonyl)amino-3-(3,4-dihydroxyphenyl)propanoate in a solvent, adding an acid to convert the (2R)-2-phenylcarbonyloxypropyl (2S)-2-(tert-butoxycarbonyl)amino-3-(3,4-dihydroxyphenyl)propanoate to (2R)-2-phenylcarbonyloxypropyl (2S)-2-amino-3-(3,4-dihydroxyphenyl)propanoate acid salt, adding methanesulfonic acid to convert the (2R)-2-phenylcarbonyloxypropyl (2S)-2-amino-3-(3,4-dihydroxyphenyl)propanoate acid salt to (2R)-2-phenylcarbonyloxypropyl (2S)-2-amino-3-(3,4-dihydroxyphenyl)propanoate mesylate, and isolating the (2R)-2-phenylcarbonyloxypropyl (2S)-2-amino-3-(3,4-dihydroxyphenyl)propanoate mesylate from the solvent, are provided.

In an eighth aspect, methods of preparing (2R)-2-phenylcarbonyloxypropyl (2S)-2-amino-3-(3,4-dihydroxyphenyl)propanoate mesylate comprising providing a solution of (2R)-2-phenylcarbonyloxypropyl (2S)-2-(tert-butoxycarbonyl)amino-3-(3,4-dihydroxyphenyl)propanoate in a solvent, adding methanesulfonic acid to convert the (2R)-2-phenylcarbonyloxypropyl (2S)-2-(tert-butoxycarbonyl)amino-3-(3,4-dihydroxyphenyl)propanoate to (2R)-2-phenylcarbonyloxypropyl (2S)-2-amino-3-(3,4-dihydroxyphenyl)propanoate mesylate, and isolating the (2R)-2-phenylcarbonyloxypropyl (2S)-2-amino-3-(3,4-dihydroxyphenyl)propanoate mesylate from the solvent, are provided.

In a ninth aspect, methods of preparing crystalline (2R)-2-phenylcarbonyloxypropyl (2S)-2-amino-3-(3,4-dihydroxyphenyl)propanoate mesylate comprising providing a solution of (2R)-2-phenylcarbonyloxypropyl (2S)-2-(tert-butoxycarbonyl)amino-3-(3,4-dihydroxyphenyl)propanoate in a first solvent, deprotecting the tert-butoxycarbonyl group with an acid to provide (2R)-2-phenylcarbonyloxypropyl (2S)-2-amino-3-(3,4-dihydroxyphenyl)propanoate acid salt, removing the first solvent and adding water to the (2R)-2-phenylcarbonyloxypropyl (2S)-2-amino-3-(3,4-dihydroxyphenyl)propanoate acid salt, neutralizing the (2R)-2-phenylcarbonyloxypropyl (2S)-2-amino-3-(3,4-dihydroxyphenyl)propanoate acid salt with a base to provide (2R)-2-phenylcarbonyloxypropyl (2S)-2-amino-3-(3,4-dihydroxyphenyl)propanoate, extracting the (2R)-2-phenylcarbonyloxypropyl (2S)-2-amino-3-(3,4-dihydroxyphenyl)propanoate with a second solvent, adding methanesulfonic acid to the extracted (2R)-2-phenylcarbonyloxypropyl (2S)-2-amino-3-(3,4-dihydroxyphenyl)propanoate to convert the (2R)-2-phenylcarbonyloxypropyl (2S)-2-amino-3-(3,4-dihydroxyphenyl)propanoate to crystalline (2R)-2-phenylcarbonyloxypropyl (2S)-2-amino-3-(3,4-dihydroxyphenyl)propanoate mesylate, and isolating the crystalline (2R)-2-phenylcarbonyloxypropyl (2S)-2-amino-3-(3,4-dihydroxyphenyl)propanoate mesylate from the second solvent, are provided.

These and other features provided by the present disclosure are set forth herein.

BRIEF DESCRIPTION OF THE DRAWINGS

The skilled artisan will understand that the drawings, described herein, are for illustration purposes only. The drawings are not intended to limit the scope provided by the present disclosure.

FIG. 6 shows an X-ray powder diffraction pattern of (2R)-2-phenylcarbonyloxypropyl (2S)-2-amino-3-(3,4-dihydroxyphenyl)propanoate mesylate crystallized from 1% water in acetonitrile.

Definitions

Figure 1:
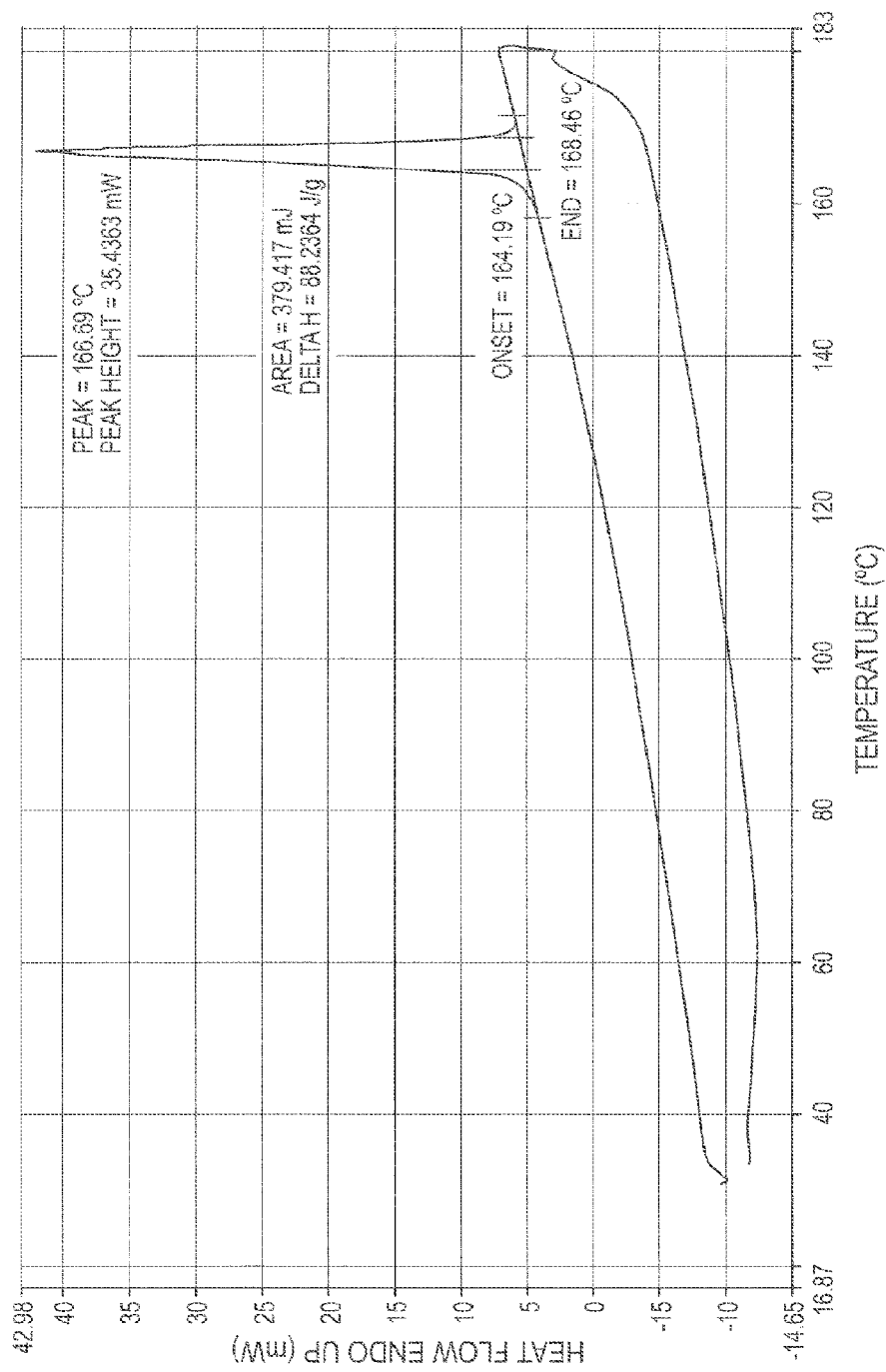
FIG. 1 shows a differential scanning calorimetry thermogram of (2R)-2-phenylcarbonyloxypropyl (2S)-2-amino-3-(3,4-dihydroxyphenyl)propanoate mesylate crystallized from isopropanol.
Figure 2:
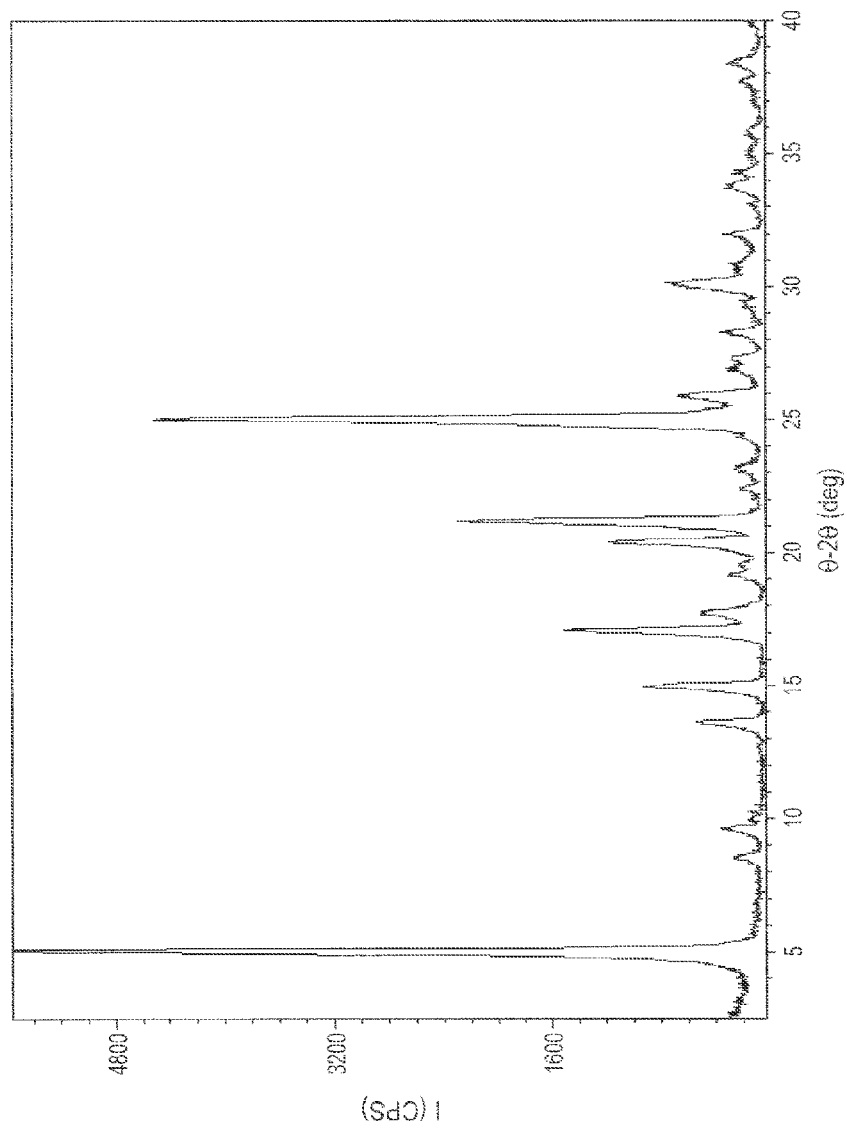
FIG. 2 shows an X-ray powder diffraction pattern of (2R)-2-phenylcarbonyloxypropyl (2S)-2-amino-3-(3,4-dihydroxyphenyl)propanoate mesylate crystallized from 1% water in isopropanol.
Figure 3:
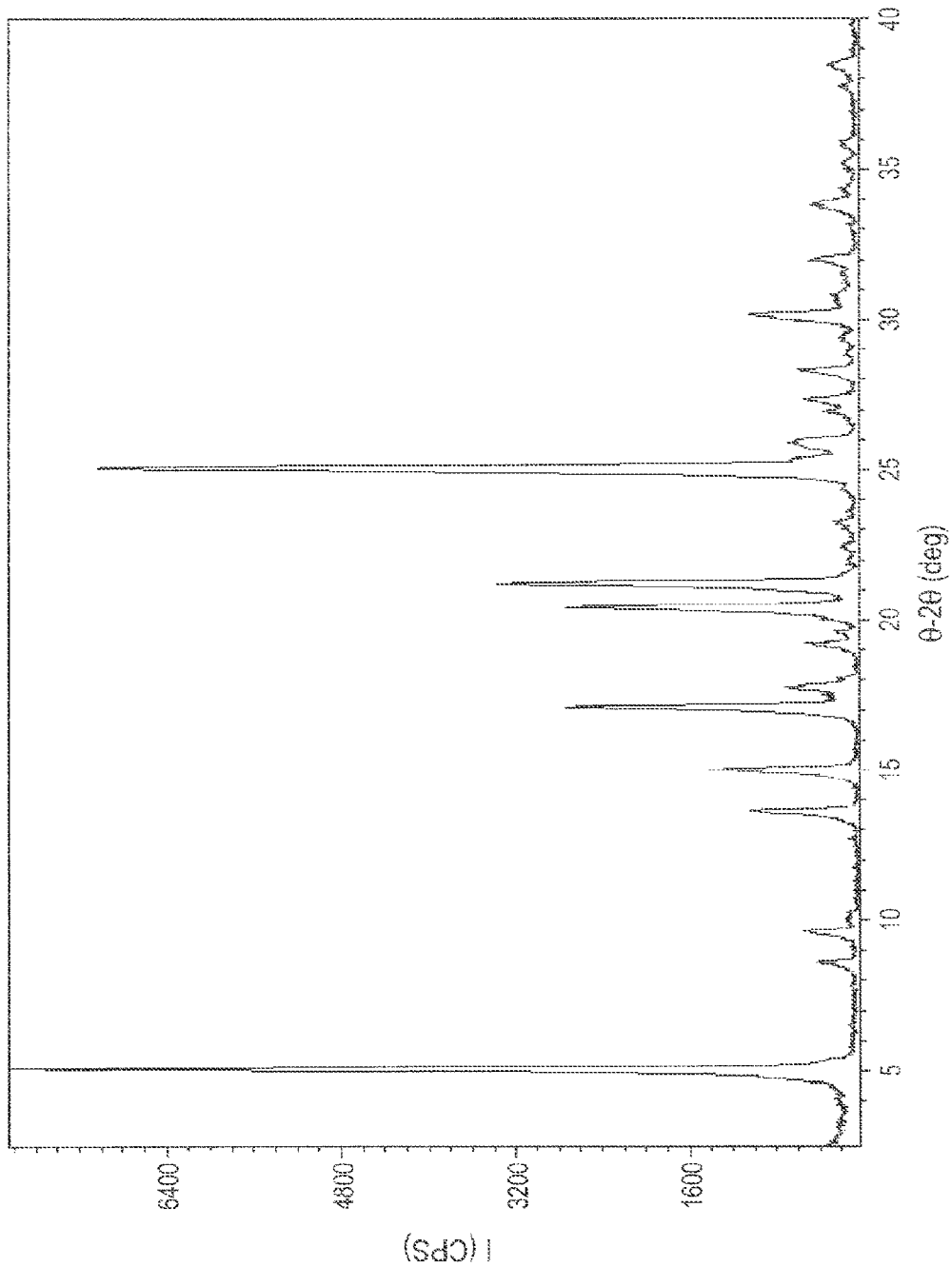
FIG. 3 shows an X-ray powder diffraction pattern of (2R)-2-phenylcarbonyloxypropyl (2S)-2-amino-3-(3,4-dihydroxyphenyl)propanoate mesylate crystallized from isopropanol.
Figure 4:
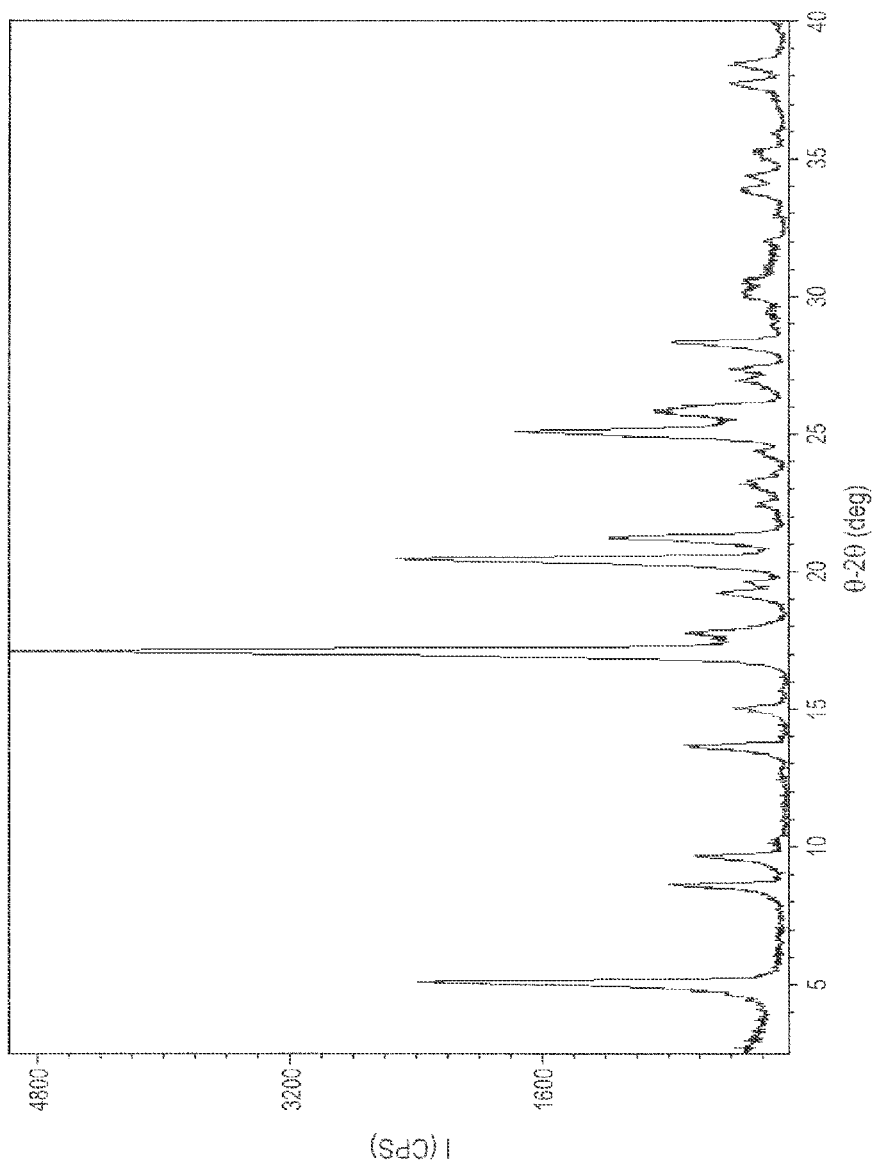
FIG. 4 shows an X-ray powder diffraction pattern of (2R)-2-phenylcarbonyloxypropyl (2S)-2-amino-3-(3,4-dihydroxyphenyl)propanoate mesylate crystallized from methanol/methyl-tert-butyl ether (1:7).
Figure 5:
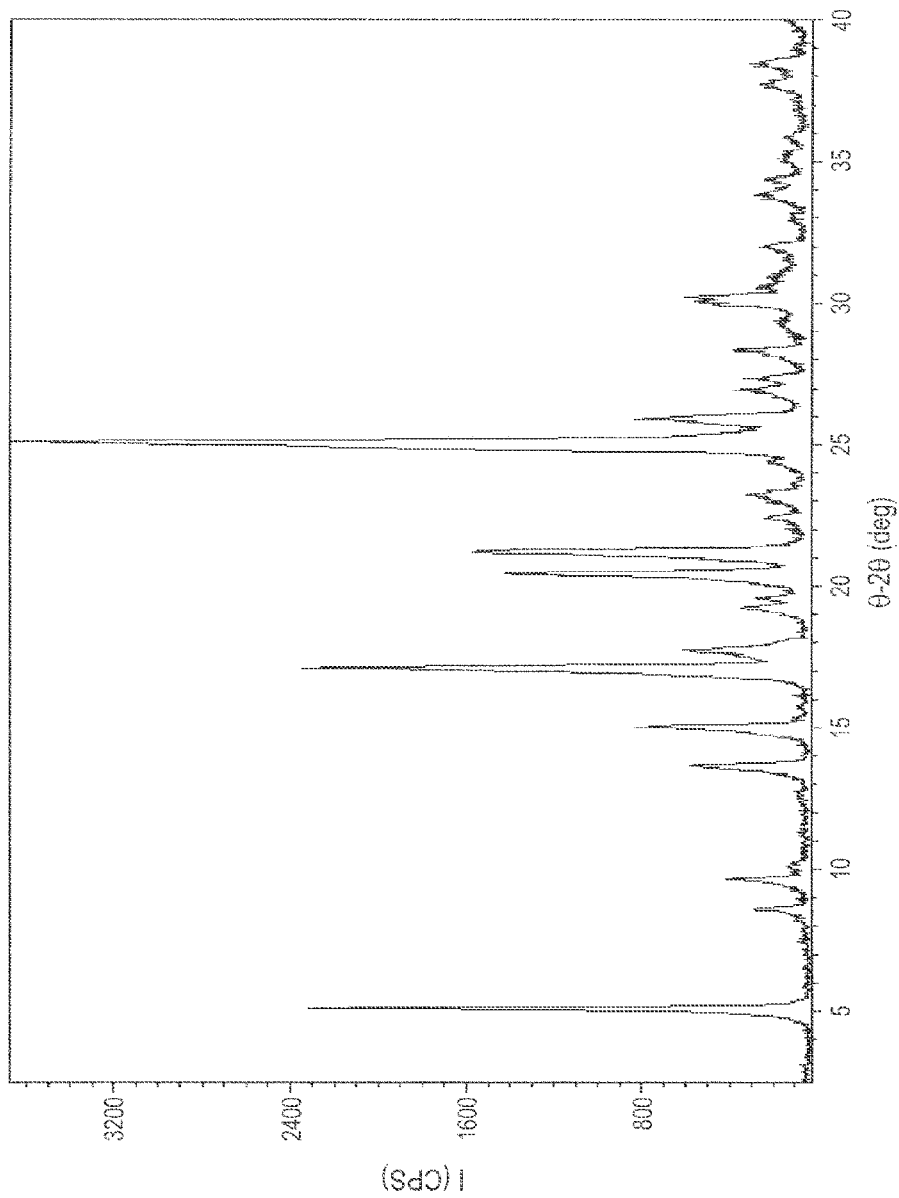
FIG. 5 shows an X-ray powder diffraction pattern of (2R)-2-phenylcarbonyloxypropyl (2S)-2-amino-3-(3,4-dihydroxyphenyl)propanoate mesylate crystallized from 0.5% water in methanol/methyl-tert-butyl ether (1:5).

"AUC" is the area under a curve representing the concentration of a compound or metabolite thereof in a biological fluid in a patient as a function of time following administration of the compound to the patient. In certain embodiments, the compound can be a prodrug and the metabolite can be a drug. Examples of biological fluids include blood and plasma. The AUC may be determined by measuring the concentration of a compound or metabolite thereof in a biological fluid such as the plasma or blood using methods such as liquid chromatography-tandem mass spectrometry (LC/NIS/MS), at various time intervals, and calculating the area under the plasma concentration-versus-time curve. Suitable methods for calculating the AUC from a drug concentration-versus-time curve are well known in the art. As relevant to the disclosure herein, an AUC for levodopa may be determined by measuring the concentration of levodopa in the plasma or blood of a patient following oral administration of a dosage form comprising (2R)-2-phenylcarbonyloxypropyl (2S)-2-amino-3-(3,4-dihydroxyphenyl)propanoate mesylate or crystalline form thereof.

"Bioavailability" refers to the amount of a drug that reaches the systemic circulation of a patient following administration of the drug or prodrug thereof to the patient and may be determined by evaluating, for example, the plasma or blood concentration-versus-time profile for a drug. Parameters useful in characterizing a plasma or blood concentration-versus-time curve include the area under the curve (AUC), the time to peak concentration ($T_{max}$), and the maximum drug concentration ($C_{max}$), where $C_{max}$ is the maximum concentration of a drug in the plasma or blood of a patient following administration of a dose of the drug or prodrug thereof to the patient, and $T_{max}$ is the time to the maximum concentration ($C_{max}$) of a drug in the plasma or blood of a patient following administration of a dose of the drug or prodrug thereof to the patient.

"Diastereomeric purity" refers to the percent of one diastereomer of a compound relative to all other diastereomers of the compound in a composition containing more than one diastereomer of the compound. For example, a composition having a diastereomeric purity of 97% of (2R)-2-phenylcarbonyloxypropyl (2S)-2-amino-3-(3,4-dihydroxyphenyl)propanoate mesylate when about 97% of the 2-phenylcarbonyloxypropyl-2-amino-3-(3,4-dihydroxyphenyl)propanoate mesylate in the composition is the (2R)-2-phenylcarbonyloxypropyl (2S)-2-amino-3-(3,4-dihydroxyphenyl)propanoate mesylate diastereomer and about 3% of the 2-phenylcarbonyloxypropyl-2-amino-3-(3,4-dihydroxyphenyl)propanoate mesylate in the composition comprises one or more of the other isomers such as the (2R)-(2R)-, the (2S)-(2R)-, and/or the (2S)-(2S)-isomers. In some embodiments, the diastereomeric purity is, for example, greater than or at least 90%, at least about 91%, at least about 92%, at least about 93%, at least about 94%, at least about 95%, at least about 96%, at least about 97%, at least about 98%, or at least about 99%.

"Levodopa prodrug mesylate" refers to (2R)-2-phenylcarbonyloxypropyl (2S)-2-amino-3-(3,4-dihydroxyphenyl)propanoate mesylate and crystalline form thereof.

"Parkinson's disease" is a clinical syndrome comprising bradykinesia (slowness and poverty of movement), muscular rigidity, resting tremor (which usually abates during voluntary movement), and an impairment of postural balance leading to disturbance of gait and falling. Other symptoms include gait and posture disturbances such as shuffling, decreased arm swing, turning "en bloc," stooped, forward-reflexed posture, festination, gait freezing and dystonia; speech and swallowing disturbances such as hypophonia, festinating speech, drooling, non-motor causes of speech/language disturbance in both expressive and receptive language, and dysphagia; as well as fatigue, masked facies, micorpgraphia, impaired fine motor dexterity and coordination, impaired gross motor coordination, and poverty of movement. Non-motor mood disturbances associated with Parkinson's disease include mood disturbances such as depression; cognitive disturbances such as slowed reaction time, executive dysfunction, dementia, memory loss, and medication effects; sleep disturbances such as excessive daytime somnolence, insomnia, and disturbances in REM sleep; sensation disturbances such as impair visual perception, dizziness and fainting, impaired proprioception, reduction or loss of sense of smell, and pain; and autonomic disturbances such as oily skin and seborxheic dermatitis, urinary incontinence, constipation and gastric dysmotility, altered sexual function, and weight loss.

The Unified Parkinson's disease Rating scale is the primary clinical tool used for the diagnosis of Parkinson's disease (see e.g., Gelb et al., *Arch Neurol* 1999, 56(1), 33-9; and Goetz, *Mov Disord* 2003, 18(7), 738-50).

"Patient" includes animals and mammals, for example humans.

"Pharmaceutical composition" refers to a composition comprising (2R)-2-phenylcarbonyloxypropyl (2S)-2-amino-3-(3,4-dihydroxyphenyl)propanoate mesylate or crystalline form thereof and at least one pharmaceutically acceptable vehicle with which the compound is administered to a patient.

"Pharmaceutically acceptable" refers to approved or approvable by a regulatory agency of a federal or a state government, listed in the U.S. Pharmacopoeia, or listed in other generally recognized pharmacopoeia for use in mammals, including humans.

"Pharmaceutically acceptable vehicle" refers to a diluent, adjuvant, excipient, or carrier with which (2R)-2-phenylcarbonyloxypropyl (2S)-2-amino-3-(3,4-dihydroxyphenyl)propanoate mesylate or crystalline form thereof is administered to a patient.

"Prodrug" refers to a derivative of a drug molecule that requires a transformation within the body to release the active drug. Prodrugs are frequently, although not necessarily, pharmacologically inactive until converted to the parent drug. A carboxyl-containing drug may be converted to, for example, an ester of either simple alkyl or acyloxyalkyl prodrug, which may be hydrolyzed in vivo to provide the carboxyl-containing drug. Prodrugs for drugs with functional groups different than those listed above are well known to those skilled in the art.

"Promoiety" refers to a form of protecting group that when used to mask a functional group within a drug converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry," (Wiley, 2$^{nd}$ ed. 1991) and Harrison et al., "Compendium of Synthetic Organic Methods," Vols. 1-8 (John Wiley and Sons, 1971-1996). Examples of amino protecting groups include, but are not limited to, formyl, acetyl, trifluoroacetyl, benzyl, benzyloxycarbonyl (Cbz), tert-butoxycarbonyl (Boc), trimethylsilyl (TMS), 2-(trimethylsilyl)ethanesulfonyl (SES), trityl and substituted trityl groups, allyloxycarbonyl, 9-fluorenylmethoxycarbonyl (FMOC), 6-nitroveratryloxycarbonyl (NVOC), and the like. Examples of hydroxy protecting groups include, but are not limited to, those where the hydroxy group is either acylated or alkylated such as benzyl, and trityl ethers as well as alkyl ethers, tetrahydropyranyl ethers, trialkylsilyl ethers, and allyl ethers.

"Sustained release" refers to release of a therapeutic or preventive amount of a drug or an active metabolite thereof over a period of time that is longer than that of a conventional formulation of the drug. For oral formulations, the term "sustained release" typically means release of the drug within the gastrointestinal tract lumen over a time period ranging from about 2 to about 30 hours, and in certain embodiments, over a time period ranging from about 4 to about 24 hours. Sustained release formulations achieve therapeutically effective concentrations of the drug in the systemic circulation over a prolonged period of time relative to that achieved by oral administration of a conventional formulation of the drug.

"Delayed release" refers to release of the drug or an active metabolite thereof into the gastrointestinal lumen after a delayed time period, for example a delay of about 1 to about 12 hours, relative to that achieved by oral administration of a conventional formulation of the drug.

"Treating" or "treatment" of a disease refers to arresting or ameliorating a disease, disorder, or at least one of the clinical symptoms of a disease or disorder. In certain embodiments, "treating" or "treatment" refers to arresting or ameliorating at least one physical parameter of the disease or disorder, which may or may not be discernible by the patient. In certain embodiments, "treating" or "treatment" refers to inhibiting or controlling the disease or disorder, either physically (e.g., stabilization of a discernible symptom), physiologically (e.g., stabilization of a physical parameter), or both. In certain embodiments, "treating" or "treatment" refers to delaying, in some cases indefinitely, the onset of a disease or disorder.

"Therapeutically effective amount" means the amount of a compound that, when administered to a patient for treating a disease in the patient, is sufficient to effect such treatment of the disease. The "therapeutically effective amount" will vary depending on the compound, the disease and its severity and the age, weight, etc., of the patient having the disease to be treated.

Reference is now be made in detail to certain embodiments of compounds, compositions, and methods. The disclosed embodiments are not intended to be limiting of the claims. To the contrary, the claims are intended to cover all alternatives, modifications, and equivalents of the disclosed embodiments.

Compounds

The levodopa prodrug, (2R)-2-phenylcarbonyloxypropyl (2S)-2-amino-3-(3,4-dihydroxyphenyl)propanoate mesylate 1:

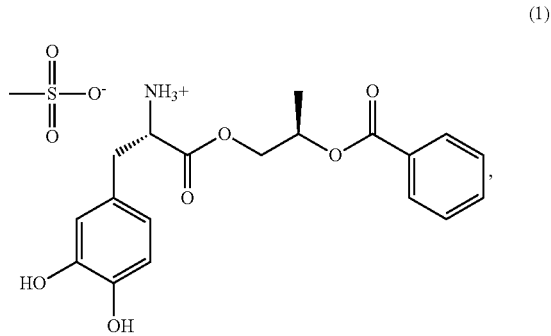

(1)

and crystalline form thereof are disclosed.

One skilled in the art will appreciate that although (2R)-2-phenylcarbonyloxypropyl (2S)-2-amino-3-(3,4-dihydroxyphenyl)propanoate mesylate is disclosed, a sample of (2R)-2-phenylcarbonyloxypropyl (2S)-2-amino-3-(3,4-dihydroxyphenyl)propanoate mesylate can have various compositional and diastereomeric purities. In certain embodiments, (2R)-2-phenylcarbonyloxypropyl (2S)-2-amino-3-(3,4-dihydroxyphenyl)propanoate mesylate or crystalline form thereof can exhibit a compositional purity of at least about 90%, at least about 91%, at least about 92%, at least about 93%, at least about 94%, at least about 95%, at least about 96%, at least about 97%, at least about 98%, at least about 99%, and in certain embodiments, in excess of at least about 99%. In certain embodiments, (2R)-2-phenylcarbonyloxypropyl (2S)-2-amino-3-(3,4-dihydroxyphenyl)propanoate mesylate or crystalline form thereof can exhibit a diastereomeric purity of at least about 90%, at least about 91%, at least about 92%, at least about 93%, at least about 94%, at least about 95%, at least about 96%, at least about 97%, at least about 98%, at least about 99%, and in certain embodiments, in excess of at least about 99%.

(2R)-2-Phenylcarbonyloxypropyl (2S)-2-amino-3-(3,4-dihydroxyphenyl)propanoate mesylate may exist in several tautomeric forms. Accordingly, all possible tautomeric forms of (2R)-2-phenylcarbonyloxypropyl (2S)-2-amino-3-(3,4-dihydroxyphenyl)propanoate mesylate are encompassed unless otherwise specified. All isotopically labeled forms of (2R)-2-phenylcarbonyloxypropyl (2S)-2-amino-3-(3,4-dihydroxyphenyl)propanoate mesylate are also encompassed unless otherwise specified. Examples of isotopes that may be incorporated into (2R)-2-phenylcarbonyloxypropyl (2S)-2-amino-3-(3,4-dihydroxyphenyl)propanoate mesylate include, but are not limited to, $^2$H, $^3$H, $^{11}$C, $^{13}$C, $^{14}$C, $^{15}$N, $^{18}$O, and $^{17}$O.

In certain embodiments, (2R)-2-phenylcarbonyloxypropyl (2S)-2-amino-3-(3,4-dihydroxyphenyl)propanoate mesylate is a crystalline form. In certain embodiments, an X-ray powder diffraction pattern of crystalline (2R)-2-phenylcarbonyloxypropyl (2S)-2-amino-3-(3,4-dihydroxyphenyl)propanoate mesylate exhibits characteristic diffraction peaks (°2θ) at 4.7±0.2, 5.0±0.2, 8.5±0.2, 9.6±0.2, 13.6±0.2, 15.0±0.2, 17.0±0.2, 17.4±0.2, 17.7±0.2, 19.1±0.2, 19.5±0.2, 20.0±0.2, 20.4±0.2, 21.1±0.2, 22.3±0.2, 22.9±0.2, 23.1±0.2, 23.3±0.2, 24.3±0.2, 25.0±0.2, 25.3±0.2, 25.7±0.2, 25.8±0.2, 26.9±0.2, 27.3±0.2, 28.2±0.2, 30.1±0.2, 30.5±0.2, 32.0±0.2, 33.8±0.2, 34.3±0.2, 37.6±0.2, and 38.4±0.2. In certain embodiments, crystalline (2R)-2-phenylcarbonyloxypropyl (2S)-2-amino-3-(3,4-dihydroxyphenyl)propanoate mesylate exhibits an X-ray powder diffraction pattern substantially as shown in any one of FIGS. 2-6.

One skilled in the art will recognize that slight variations in the observed °2θ diffraction angles can be expected based on, for example, the specific diffractometer employed, the analyst, and the sample preparation technique. Greater variation can be expected for the relative peak intensities. Comparison of diffraction patterns can be based primarily on observed °2θ diffraction angles with lesser importance attributed to relative peak intensities. Diffraction patterns demonstrating the variations in the observed °2θ diffraction angles and peak intensities for crystalline (2R)-2-phenylcarbonyloxypropyl (2S)-2-amino-3-(3,4-dihydroxyphenyl)propanoate mesylate crystallized from different solvents is shown in FIGS. 2-6. For the X-ray powder diffraction patterns shown in FIGS. 2-6, the peaks that generally exhibit the most intensity are located at °2θ diffraction angles of 5.0±0.2, 8.5±0.2, 13.6±0.2, 15.0±0.2, 17.0±0.2, 17.7±0.2, 20.4±0.2, 21.1±0.2, 25.0±0.2, 25.8±0.2, 28.2±0.2, 30.1±0.2, and 37.6±0.2. An X-ray powder diffraction pattern that exhibits characteristic diffraction peaks (°2θ) at 5.0±0.2, 8.5±0.2, 13.6±0.2, 15.0±0.2, 17.0±0.2, 17.7±0.2, 20.4±0.2, 21.1±0.2, 25.0±0.2, 25.8±0.2, 28.2±0.2, 30.1±0.2, and 37.6±0.2 will be substantially the same as the X-ray powder diffraction pattern of crystalline (2R)-2-phenylcarbonyloxypropyl (2S)-2-amino-3-(3,4-dihydroxyphenyl)propanoate mesylate.

In certain embodiments, crystalline (2R)-2-phenylcarbonyloxypropyl (2S)-2-amino-3-(3,4-dihydroxyphenyl)propanoate mesylate exhibits a melting point from about 157° C. to about 162° C.

In certain embodiments, crystalline (2R)-2-phenylcarbonyloxypropyl (2S)-2-amino-3-(3,4-dihydroxyphenyl)propanoate mesylate is characterized by a differential scanning calorimetry (DSC) thermogram having an endothermic peak at about 164.5° C., and in certain embodiments at about 164.5±2.5° C. An example of a DSC thermogram of crystalline (2R)-2-phenylcarbonyloxypropyl (2S)-2-amino-3-(3,4-dihydroxyphenyl)propanoate mesylate is shown in FIG. 1.

In certain embodiments, crystalline (2R)-2-phenylcarbonyloxypropyl (2S)-2-amino-3-(3,4-dihydroxyphenyl)propanoate mesylate is stable, e.g., does not absorb moisture and/or convert to another isomorphic form under typical pharmaceutical processing and/or storage conditions.

The physical properties and characteristics of crystalline (2R)-2-phenylcarbonyloxypropyl (2S)-2-amino-3-(3,4-dihydroxyphenyl)propanoate mesylate prepared by methods provided by the present disclosure are consistent with that of a single isomorph. By contrast, crystalline (2R)-2-phenylcarbonyloxypropyl (2S)-2-amino-3-(3,4-dihydroxyphenyl)propanoate hydrochloride prepared by similar methods can exhibit three isomorphic forms. The environmental stability of the single isomorphic form of crystalline (2R)-2-phenylcarbonyloxypropyl (2S)-2-amino-3-(3,4-dihydroxyphenyl)propanoate mesylate recommends its use in pharmaceutical compositions.

Synthesis (2R)-2-Phenylcarbonyloxypropyl (2S)-2-amino-3-(3,4-dihydroxyphenyl)propanoate mesylate 1 can be prepared via the synthetic method illustrated in Scheme 1.

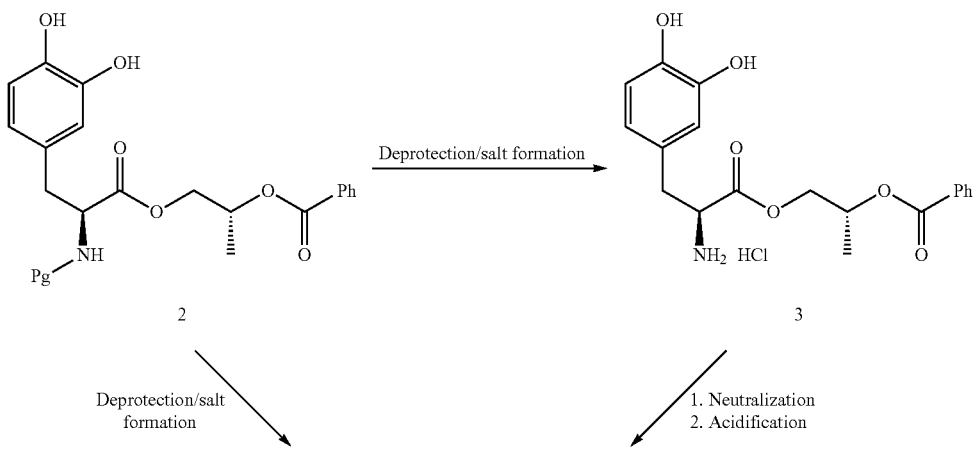

-continued

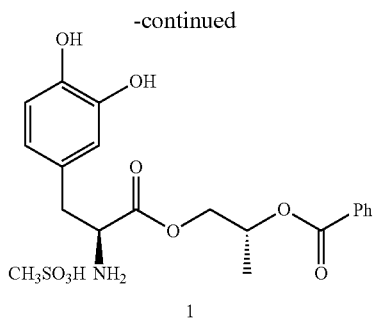

1

Starting materials useful for preparing these compounds and intermediates thereof are commercially available or can be prepared by well-known synthetic methods (Harrison et al., "Compendium of Synthetic Organic Methods," Vols. 1-8, John Wiley and Sons, 1971-1996; "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; and Paquette, "Encyclopedia of Reagents for Organic Synthesis," John Wiley & Sons, 1995). Methods of synthesizing carboxyl ester levodopa prodrugs are described-in Xiang et al., U.S. Application Publication Nos. 2005/0282891 and 2006/0020028, each of which is incorporated herein by reference in its entirety. Other methods for synthesizing (2R)-2-phenylcarbonyloxypropyl (2S)-2-amino-3-(3,4-dihydroxyphenyl) propanoate mesylate will be readily apparent to one skilled in the art. Accordingly, the method presented in Scheme 1 is illustrative rather than comprehensive.

For example, (2R)-2-phenylcarbonyloxypropyl (2S)-2-amino-3-(3,4-dihydroxyphenyl)propanoate mesylate 1 can be prepared from the corresponding appropriately protected (2R)-2-phenylcarboxyloxypropyl (2S)-2-amino-3-(3,4-dihydroxyphenyl)propanoate precursor 2 via a direct or an indirect route as shown in Scheme 1.

When Pg is Boc (tert-butoxycarbonyl), treatment of precursor 2 with an appropriate acid such as hydrochloric acid in an organic solvent in which precursor 2 is soluble such as, for example, dioxane, dichloromethane, tetrahydrofuran, or combinations of any of the foregoing at room temperature, followed by solvent removal and crystallization of the resulting residue using an appropriate solvent such as acetonitrile, can provide the hydrochloride salt 3. Other appropriate acids include volatile acids such as trifluoroacetic acid and hydrogen bromide. Conversion of the hydrochloride salt 3 to the corresponding mesylate salt 1 can be accomplished by neutralizing the hydrochloride salt with an appropriate base such as sodium bicarbonate ($NaHCO_3$) or potassium bicarbonate ($KHCO_3$) in an appropriate solvent such as water/dichloromethane (DCM), separating DCM from the water, and adding methanesulfonic acid to the DCM solution. The mesylate salt 1 can precipitate from the DCM.

In certain embodiments, precursor 2 can be directly converted to the mesylate salt 1 by treating precursor 2 with an excess of methanesulfonic acid, e.g., 1.1-100 equivalents, in an organic solvent in which precursor 2 is soluble such as dioxane, dichloromethane, ethylacetate, methyl tert-butyl ether, tetrahydrofuran, or mixtures of any of the foregoing at a temperature from about 20° C. to about 100° C. The mesylate salt 1 can then be precipitated out in a non-polar solvent such as methyl tert-butyl ether (MTBE), dichloromethane, or mixtures of the foregoing.

In certain embodiments, precursor 2 can be converted to the mesylate salt 1 using a one-pot procedure by treating precursor 2 with an excess of hydrogen chloride in dioxane to produce the deprotected hydrochloride salt 3, and then adding methanesulfonic acid to convert the hydrochloride salt 3 to the mesylate salt 1.

The mesylate salt 1 can be crystallized from a solvent in which the mesylate salt 1 is soluble and in which the solubility of the mesylate salt 1 is temperature dependent, such as isopropanol, methanol/MTBE, 1% water in isopropanol, 1% water in acetonitrile, or 3% water in ethylacetate, to provide the crystalline mesylate salt 1. In certain embodiments, the solvent used for crystallizing the mesylate salt 1 can be selected from acetonitrile, methanol, ethanol, isopropanol, MTBE, dioxane, acetone, ethylacetate, ethylformate, hexane, dichloromethane, and mixtures of any of the foregoing. In certain solvent mixtures comprising two solvents, the ratio of the two solvents can range from about 1:10 to about 10:1. In certain embodiments, the solvent can further comprise less than about 10% water by volume, and in certain embodiments, less than about 5% water by volume. In certain embodiments, the solvent used for crystallizing the mesylate salt 1 can comprise a mixture of methanol and MTBE in which the ratio (v/v) of methanol to MTBE is from about 1:5 to about 1:7. In certain embodiments, the solvent used for crystallizing the mesylate salt 1 can comprise from about 1% to about 4% by volume water in isopropanol. Examples of useful solvents for crystallizing the mesylate salt 1 are disclosed in Table 1.

To prepare crystalline mesylate salt 1, a solvent in which the solubility of the mesylate salt 1 is temperature dependent and mesylate salt 1, can be heated to provide a solution. In certain embodiments, the solvent can be heated to a temperature up to the reflux temperature, and in certain embodiments, up to a temperature less than 75° C. In certain embodiments, the concentration of the mesylate salt 1 in the solution is less than about 500 mg/mL and in certain embodiments is from about 50 mg/mL to about 200 mg/mL. The temperature of the solution can then be changed to decrease the solubility of the mesylate salt 1 in the solvent. For example, the temperature of the solution can be decreased to room temperature (e.g., about 25° C.), and in certain embodiments to 0° C. The time to cool the solution can be selected to optimize the yield, compositional purity, and/or optical purity of the crystalline mesylate salt 1. In some embodiments, the solution can be cooled to a first temperature and the crystalline mesylate salt 1 isolated, and the solution cooled further in a second crystallization and additional crystalline mesylate salt 1 isolated. Crystalline mesylate salt 1 can be isolated from the solvent by filtration. The filter cake can be washed in an appropriate solvent, such as, for example, a low boiling point solvent that minimizes the amount of residue remaining in the crystalline mesylate salt 1. Examples of appropriate wash solvents include acetonitrile, methanol, ethanol, isopropanol, MTBE, dioxane, acetone, ethylacetate, ethylformate, hexane, dichloromethane, and mixtures of any of the foregoing. One skilled in the art can appreciate that other methods can be used to crystallize the mesylate salt 1, including, for example, methods comprising stirring and/or seeding.

In certain embodiments, crystalline mesylate salt 1 obtained via any of the preceding methods is characterized by an X-ray powder diffraction pattern having peaks (° 2θ) at 4.7±0.2, 5.0±0.2, 8.5±0.2, 9.6±0.2, 13.6±0.2, 15.0±0.2, 17.0±0.2, 17.4±0.2, 17.7±0.2, 19.1±0.2, 19.5±0.2, 20.0±0.2, 20.4±0.2, 21.1±0.2, 22.3±0.2, 22.9±0.2, 23.1±0.2, 23.3±0.2, 24.3±0.2, 25.0±0.2, 25.3±0.2, 25.7±0.2, 25.8±0.2, 26.9±0.2, 27.3±0.2, 28.2±0.2, 30.1±0.2, 30.5±0.2, 32.0±0.2, 33.8±0.2, 34.3±0.2, 37.6±0.2, and 38.4±0.2. In certain embodiments, crystalline mesylate salt 1 obtained via any of the preceding methods is characterized by an X-ray powder diffraction pattern having major peaks (°2θ) at 5.0±0.2, 8.5±0.2, 13.6±0.2, 15.0±0.2, 17:0±0.2, 17.7±0.2, 20.4±0.2, 21.1±0.2, 25.0±0.2, 25.8±0.2, 28.2±0.2, 30.1±0.2, and 37.6±0.2.

In certain embodiments, formation and crystallization of the mesylate salt 1 can be performed in a one-pot procedure at about room temperature, e.g., 25° C. For example, after deprotection and neutralization, (2R)-2-phenylcarbonyloxypropyl (2S)-2-amino-3-(3,4-dihydroxyphenyl)propanoate can be dissolved in a solvent such as ethylacetate, isopropanol/dichloromethane, or isopropanol/ethylacetate and treated with 0.9-1.2 equivalents of methanesulfonic acid at ambient temperature. The mesylate salt 1 can crystallize from the solution with or without stirring or seeding.

As an example of the one-pot procedure for preparing crystalline (2R)-2-phenylcarbonyloxypropyl (2S)-2-amino-3-(3,4-dihydroxyphenyl)propanoate mesylate, a solution of (2R)-2-phenylcarbonyloxypropyl (2S)-2-(tert-butoxycarbonyl)amino-3-(3,4-dihydroxyphenyl)propanoate in a solvent in which it is soluble is prepared. Examples of suitable solvents include dichloromethane and dioxane. The tert-butoxycarbonyl group is deprotected by adding an acid to provide (2R)-2-phenylcarbonyloxypropyl (2S)-2-amino-3-(3,4-dihydroxyphenyl)propanoate acid salt. Suitable acids are not limited to volatile acids. Examples of suitable acids for deprotecting the tert-butoxycarbonyl group include hydrochloric acid, methanesulfonic acid, trifluoroacetic acid, and hydrogen bromide. After deprotection, the first solvent can be removed and water added to the (2R)-2-phenylcarbonyloxypropyl (2S)-2-amino-3-(3,4-dihydroxyphenyl)propanoate acid salt. The (2R)-2-phenylcarbonyloxypropyl (2S)-2-amino-3-(3,4-dihydroxyphenyl)propanoate acid salt can be neutralized with a base such as $NaHCO_3$ or $KHCO_3$ to provide (2R)-2-phenylcarbonyloxypropyl (2S)-2-amino-3-(3,4-dihydroxyphenyl)propanoate. (2R)-2-Phenylcarbonyloxypropyl (2S)-2-amino-3-(3,4-dihydroxyphenyl)propanoate can then be extracted with a second solvent such as methyl tert-butylether, dichloromethane, ethylacetate, or a mixture of ethylacetate and isopropanol. Methanesulfonic acid can be added to the extracted (2R)-2-phenylcarbonyloxypropyl (2S)-2-amino-3-(3,4-dihydroxyphenyl)propanoate to convert the (2R)-2-phenylcarbonyloxypropyl (2S)-2-amino-3-(3,4-dihydroxyphenyl)propanoate to crystalline (2R)-2-phenylcarbonyloxypropyl (2S)-2-amino-3-(3,4-dihydroxyphenyl)propanoate mesylate. Crystalline (2R)-2-phenylcarbonyloxypropyl (2S)-2-amino-3-(3,4-dihydroxyphenyl)propanoate mesylate can then be isolated from the second solvent by filtration.

One skilled in the art will appreciate that the methods provided by the present disclosure can be used to prepare (2R)-2-phenylcarbonyloxypropyl (2S)-2-amino-3-(3,4-dihydroxyphenyl)propanoate mesylate 1 or crystalline form thereof having high compositional and diastereomeric purity. For example, in certain embodiments, the compositional purity of the mesylate salt 1 can be at least about 95%, in certain embodiments, at least about 97%, in certain embodiments, at least about 98%, and in certain embodiments, can be at least about 99%, and in certain embodiments, the diastereomeric purity can be at least about 95%, in certain embodiments, at least about 97%, in certain embodiments, at least about 98%, and in certain embodiments, at least about 99%.

Uses

Levodopa prodrugs are precursors of dopamine. Thus, levodopa prodrug mesylate provided by the present disclosure may be administered to a patient suffering from any disease or disorder for which the parent drug, levodopa, is known or hereafter discovered to be therapeutically effective. Levodopa prodrug mesylate may be administered to a patient, such as a human, to treat a disease or disorder such as Parkinson's disease. The methods comprise administering to a patient in need of such treatment a therapeutically effective amount of levodopa prodrug mesylate. In therapeutic methods provided by the present disclosure, a therapeutically effective amount of levodopa prodrug mesylate may be administered to a patient suffering from a disease such as Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, or excessive daytime sleepiness. In prophylactic methods provided by the present disclosure a therapeutically effective amount of levodopa prodrug mesylate may be administered to a patient at risk of developing a disease such as Parkinson's disease, depression, attention deficit disorder; schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, or excessive daytime sleepiness.

In certain embodiments, levodopa prodrug mesylate or pharmaceutical composition thereof may be co-administered with another therapeutic agent or drug, such as a decarboxylase inhibitor or a prodrug thereof, which may act as a protectant to inhibit or prevent premature decarboxylation of the levodopa prodrug mesylate and/or the levodopa metabolite.

Levodopa prodrug mesylate may be delivered from the same dosage form as the L-aromatic amino acid decarboxylase inhibitor or from a different dosage form. Levodopa prodrug mesylate may be administered at the same time as, prior to, or subsequent to, the administration of a decarboxylase inhibitor. Levodopa prodrug mesylate together with a decarboxylase inhibitor or decarboxylase inhibitor prodrug or derivative can be administered to a patient, such as a human, to treat a disease or disorder such as Parkinson's disease.

In certain embodiments, levodopa prodrug mesylate or pharmaceutical composition thereof together with at least one decarboxylase inhibitor or at least one decarboxylase inhibitor prodrug or derivative may be advantageously used in human medicine. In certain embodiments, levodopa prodrug mesylate or pharmaceutical composition thereof may be useful for the treatment of Parkinson's disease. When used to treat Parkinson's disease, levodopa prodrug mesylate or pharmaceutical composition thereof may be administered or applied in combination with a decarboxylase inhibitor such as carbidopa, a carbidopa prodrug, benserazide, and/or a benserazide prodrug. Additionally, the therapeutic effectiveness of the above combinations may be enhanced by co-administration of another pharmaceutically active agent such as a catechol-O-methyltransferase (COMT) inhibitor such as entacapone, an entacapone prodrug, tolecapone, and/or a tolecapone prodrug. Further, in certain embodiments, levodopa prodrug mesylate of pharmaceutical composition thereof may be administered to a patient, such as a human, together with (i) a decarboxylase inhibitor such as carbidopa, a carbidopa prodrug, benserazide, or a benserazide prodrug, and (ii) a pharmaceutically active agent such as a COMT inhibitor or prodrug thereof, to treat a disease or disorder such as Parkinson's disease.

(2R)-2-Phenylcarbonyloxypropyl (2S)-2-amino-3-(3,4-dihydroxyphenyl)propanoate mesylate may be included in a pharmaceutical composition and/or dosage form adapted for oral administration, although (2R)-2-phenylcarbonyloxypropyl (2S)-2-amino-3-(3,4-dihydroxyphenyl)propanoate mesylate may also be administered by any other convenient route, such as for example, by injection, infusion, inhalation, transdermal, or absorption through epithelial or mucosal membranes (e.g., oral, rectal, and/or intestinal mucosa).

(2R)-2-Phenylcarbonyloxypropyl (2S)-2-amino-3-(3,4-dihydroxyphenyl)propanoate mesylate or pharmaceutical compositions thereof may provide therapeutic or prophylactic plasma and/or blood concentrations of levodopa following oral administration to a patient. The carboxyl ester promoiety of (2R)-2-phenylcarbonyloxypropyl (2S)-2-amino-3-(3,4-dihydroxyphenyl)propanoate mesylate may be cleaved in vivo either chemically and/or enzymatically to release the parent drug, levodopa. One or more enzymes present in the stomach, intestinal lumen, intestinal tissue, blood, liver, brain, or any other suitable tissue of a patient may enzymatically cleave the promoiety of the administered compounds. For example, the carboxyl ester promoiety of (2R)-2-phenylcarbonyloxypropyl (2S)-2-amino-3-(3,4-dihydroxyphenyl)propanoate mesylate may be cleaved prior to absorption from the gastrointestinal tract (e.g., within the stomach or intestinal lumen) and/or after absorption from the gastrointestinal tract (e.g., in intestinal tissue, blood, liver, or other suitable tissue of a mammal). In certain embodiments, (2R)-2-phenylcarbonyloxypropyl (2S)-2-amino-3-(3,4-dihydroxyphenyl)propanoate mesylate may be actively transported across the intestinal endothelium by organic cation transporters expressed throughout the gastrointestinal tract including the small intestine and colon. Levodopa may remain conjugated to the carboxyl ester promoiety during transit across the intestinal mucosal barrier to prevent or minimize presystemic metabolism. In certain embodiments, (2R)-2-phenylcarbonyloxypropyl (2S)-2-amino-3-(3,4-dihydroxyphenyl)propanoate mesylate is essentially not metabolized to levodopa within gastrointestinal enterocytes, but is metabolized to levodopa within the systemic circulation, for example in the plasma. In such embodiments, (2R)-2-phenylcarbonyloxypropyl (2S)-2-amino-3-(3,4-dihydroxyphenyl)propanoate mesylate may be absorbed into the systemic circulation from the small and large intestines either by active transport, passive diffusion, or by both active and passive processes. Cleavage of the promoiety from (2R)-2-phenylcarbonyloxypropyl (2S)-2-amino-3-(3,4-dihydroxyphenyl)propanoate mesylate after absorption from the gastrointestinal tract may allow the levodopa prodrug mesylate to be absorbed into the systemic circulation either by active transport, passive diffusion, or by both active and passive processes. The mechanism of cleavage is not important to the present embodiments. For example, the carboxyl ester promoiety can be cleaved after absorption from the gastrointestinal tract, for example, in intestinal tissue, blood, liver, or other suitable tissue of a mammal.

(2R)-2-Phenylcarbonyloxypropyl (2S)-2-amino-3-(3,4-dihydroxyphenyl)propanoate mesylate may be administered in similar amounts and using a similar schedule as described in the art for levodopa. For example, (2R)-2-phenylcarbonyloxypropyl (2S)-2-amino-3-(3,4-dihydroxyphenyl)propanoate mesylate can be useful in treating Parkinson's disease by administration of (2R)-2-phenylcarbonyloxypropyl (2S)-2-amino-3-(3,4-dihydroxyphenyl)propanoate mesylate together with a decarboxylase inhibitor such as carbidopa or a prodrug of carbidopa, in certain embodiments by the oral route, to a mammalian subject in need of the treatment. In a human subject weighing about 70 kg, (2R)-2-phenylcarbonyloxypropyl (2S)-2-amino-3-(3,4-dihydroxyphenyl)propanoate mesylate can be administered at a dose over time having an equivalent weight of levodopa of from about 10 mg to about 10 g per day, and in certain embodiments, an equivalent weight of levodopa of from about 100 mg to about 3 g per day. A dose of (2R)-2-phenylcarbonyloxypropyl (2S)-2-amino-3-(3,4-dihydroxyphenyl)propanoate mesylate taken at any one time can have an equivalent weight of levodopa of from about 10 mg to about 3 g. A dose can be adjusted by one skilled in the art based on several factors, including, for example, the body weight and/or condition of the subject treated, the dose of the decarboxylase inhibitor or prodrug of a decarboxylase inhibitor being administered, the severity of the disease being treated, the incidence of side effects, the manner of administration, and the judgment of the prescribing physician. Dosage ranges may be determined by methods known to one skilled in the art.

(2R)-2-Phenylcarbonyloxypropyl (2S)-2-amino-3-(3,4-dihydroxyphenyl)propanoate mesylate may be assayed in vitro and in vivo for the desired therapeutic or prophylactic activity prior to use in humans. For example, in vitro assays may be used to determine whether administration of (2R)-2-phenylcarbonyloxypropyl (2S)-2-amino-3-(3,4-dihydroxyphenyl)propanoate mesylate is a substrate of a transporter protein, including organic cation transporters such as OCTN1 and OCTN2. Examples of certain assay methods applicable to analyzing the ability of (2R)-2-phenylcarbonyloxypropyl (2S)-2-amino-3-(3,4-dihydroxyphenyl)propanoate mesylate to act as a substrate for a transporter protein are disclosed in Zerangue et al., U.S. Application Publication No. 2003/0158254, which is incorporated herein by reference in its entirety. In vivo assays may also be used to determine whether administration of (2R)-2-phenylcarbonyloxypropyl (2S)-2-amino-3-(3,4-dihydroxyphenyl)propanoate mesylate is therapeutically effective. (2R)-2-Phenylcarbonyloxypropyl (2S)-2-amino-3-(3,4-dihydroxyphenyl)propanoate mesylate may also be demonstrated to be effective and safe using animal model systems.

In certain embodiments, a therapeutically effective dose of (2R)-2-phenylcarbonyloxypropyl (2S)-2-amino-3-(3,4-dihydroxyphenybpropanoate mesylate may provide therapeutic benefit without causing substantial toxicity. Toxicity of (2R)-2-phenylcarbonyloxypropyl (2S)-2-amino-3-(3,4-dihydroxyphenyl)propanoate mesylate may be determined using standard pharmaceutical procedures and may be ascertained by one skilled in the art. The dose ratio between toxic and therapeutic effect is the therapeutic index. A dosage of (2R)-2-phenylcarbonyloxypropyl (2S)-2-amino-3-(3,4-dihydroxyphenyl)propanoate mesylate may be within a range capable of establishing and maintaining a therapeutically effective circulating plasma and/or blood concentration of levodopa that exhibits little or no toxicity.

In addition to the use of (2R)-2-phenylcarbonyloxypropyl (2S)-2-amino-3-(3,4-dihydroxyphenyl)propanoate mesylate and compositions comprising (2R)-2-phenylcarbonyloxypropyl (2S)-2-amino-3-(3,4-dihydroxyphenyl)propanoate mesylate provided by the present disclosure for treating Parkinson's disease, levodopa prodrugs mesylate and compositions thereof may also be useful for treating other dopamine-related diseases. Dopamine-related diseases can be characterized by either insufficient or excessive functional dopaminergic activity in the central nervous system. Examples of other dopamine-related diseases include, but are not limited to, affective disorders such as depression and attention deficit disorder, psychotic disorders such as schizophrenia and manic depression, cognitive impairment disorders such as mild cognitive impairment, movement disorders such as restless legs syndrome, periodic limb movement disorders, tardive dyskinesia, hypertension, Huntington's disease, and Tourette's syndrome, addictive disorders such as alcohol addiction or abuse, nicotine addiction or abuse, and drug addiction and abuse, congestive heart failure, and excessive daytime sleepiness. For the treatment of these and other dopamine-related diseases, (2R)-2-phenylcarbonyloxypropyl (2S)-2-amino-3:(3,4-dihydroxyphenyl)propanoate mesylate may be co-administered with an additional active agent such as, for example, a decarboxylase inhibitor and/or a COMT inhibitor. Therapeutically effective doses for treating dopamine-related diseases may be determined by the methods disclosed herein for the treatment of Parkinson's disease and/or by methods known in the art.

Pharmaceutical Compositions

Pharmaceutical compositions provided by the present disclosure may comprise a therapeutically effective amount of (2R)-2-phenylcarbonyloxypropyl (2S)-2-amino-3-(3,4-dihydroxyphenyl)propanoate mesylate, and in certain embodiments, in purified form, together with a suitable amount of one or more pharmaceutically acceptable vehicles, so as to provide a composition for proper administration to a patient. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions may also contain wetting agents, emulsifying agents, and/or pH buffering agents. In addition, auxiliary, stabilizing, thickening, lubricating, and/or coloring agents may be used. In certain embodiments, pharmaceutical compositions may be in the form of a capsule (see e.g., Grosswald et al., U.S. Pat. No. 5,698,155). Other examples of suitable pharmaceutical vehicles are described in the art (see, for example, "Remington's Pharmaceutical Sciences," Lippincott Williams & Wilkins, 21st Edition, 2005).

Pharmaceutical compositions comprising (2R)-2-phenylcarbonyloxypropyl (2S)-2-amino-3-(3,4-dihydroxyphenyl) propanoate mesylate or crystalline form thereof may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of levodopa prodrug mesylate or crystalline form thereof and one or more pharmaceutically acceptable vehicles into formulations that can be used pharmaceutically. Proper formulation is dependent upon the route of administration chosen. In certain embodiments, a pharmaceutical composition comprising levodopa prodrug mesylate or crystalline form thereof may be formulated for oral administration, and in certain embodiments for sustained release oral administration. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for use.

Oral Pharmaceutical Compositions

In certain embodiments, (2R)-2-phenylcarbonyloxypropyl (2S)-2-amino-3-(3,4-dihydroxyphenyl)propanoate mesylate may be incorporated into pharmaceutical compositions to be administered orally. Oral administration of such pharmaceutical compositions may result in uptake of the (2R)-2-phenylcarbonyloxypropyl (2S)-2-amino-3-(3,4-dihydroxyphenyl) propanoate mesylate throughout the intestine and entry into the systemic circulation. Such compositions may be prepared in a manner known in the pharmaceutical art and comprise (2R)-2-phenylcarbonyloxypropyl (2S)-2-amino-3-(3,4-dihydroxyphenyl)propanoate mesylate and at least one pharmaceutically acceptable vehicle. Pharmaceutical compositions may include a therapeutically effective amount of (2R)-2-phenylcarbonyloxypropyl (2S)-2-amino-3-(3,4-dihydroxyphenyl)propanoate mesylate, in some embodiments, in purified form, together with a decarboxylase inhibitor such as carbidopa, a carbidopa prodrug, benserazide, or a benserazide prodrug, and a suitable amount of a pharmaceutically acceptable vehicle, so as to provide an appropriate form for administration to a patient.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, in tablet or pill forms, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds and pharmaceutical compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral pharmaceutical compositions may include standard vehicles such as mannitol, lactose, starch, magnesium stearate, sodium saccharine, cellulose, magnesium carbonate, etc. Such vehicles may be of pharmaceutical grade.

For oral liquid preparations such as suspensions, elixirs and solutions, can include suitable carriers, excipients, or diluents include water, saline, alkylene glycols (e.g., propylene glycol), polyalkylene glycols (e.g., polyethylene glycol) oils, alcohols, slightly acidic buffers from about pH 4 to about pH 6 (e.g., acetate, citrate, ascorbate from about 5 mM to about 50 mM), etc. Additionally, flavoring agents, preservatives, coloring agents, bile salts, acylcarnitines, and the like may be added.

Certain embodiments also include compositions that comprise, as the active ingredient, (2R)-2-phenylcarbonyloxypropyl (2S)-2-amino-3-(3,4-dihydroxyphenyl)propanoate mesylate associated with at least one pharmaceutically acceptable vehicle including excipients, carriers, diluents and/or adjuvants. In forming the compositions, (2R)-2-phenylcarbonyloxypropyl (2S)-2-amino-3-(3,4-dihydroxyphenyl)propanoate mesylate may be mixed with an excipient, diluted by a diluent or enclosed within a carrier, which can be in the form of a capsule, sachet, paper or other container. When an excipient serves as a diluent, it can be a solid, semi-solid, or liquid material, which can act as a vehicle, carrier, or medium for (2R)-2-phenylcarbonyloxypropyl (2S)-2-amino-3-(3,4-dihydroxyphenyl)propanoate mesylate. Thus, compositions may be in the form of tablets, pills, powders, lozenges, sachets, cachets, elixirs, suspensions, emulsions, solutions, and syrups containing, for example, up to about 90% by weight of (2R)-2-phenylcarbonyloxypropyl (2S)-2-amino-3-(3,4-dihydroxyphenyl)propanoate mesylate using, for example, soft and hard gelatin capsules.

In preparing a composition, it may be useful to mill (2R)-2-phenylcarbonyloxypropyl (2S)-2-amino-3-(3,4-dihydroxyphenyl)propanoate mesylate to provide an appropriate particle size prior to combining with other ingredients. The milled particle size of (2R)-2-phenylcarbonyloxypropyl (2S)-2-amino-3-(3,4-dihydroxyphenyl)propanoate mesylate may be adjusted depending on the aqueous solubility, and in certain embodiments, may be less than about 200 mesh and in certain embodiments, about 40 mesh. Examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methylcellulose. Compositions may additionally include lubricating agents such as talc, magnesium stearate, and mineral oil, wetting agents, emulsifying and suspending agents, preserving agents such as methyl- and propylhydroxy-benzoates, sweetening agents, pH adjusting and buffering agents, toxicity adjusting agents, flavoring agents, and the like. The compositions may be formulated so as to provide quick, sustained, or delayed release of (2R)-2-phenylcarbonyloxypropyl (2S)-2-amino-3-(3,4-dihydroxyphenyl)propanoate mesylate after administration to the patient by employing procedures known in the art.

A composition may be formulated in unit dosage form, each dosage comprising an equivalent weight of levodopa ranging from about 10 mg to about 10 g. Unit dosage form refers to a physically discrete unit suitable as a unitary dosage for humans and other mammals, each unit containing a predetermined quantity of active material calculated to produce an intended therapeutic effect, in association with a suitable pharmaceutical excipient, diluent, carrier and/or adjuvant.

(2R)-2-Phenylcarbonyloxypropyl (2S)-2-amino-3-(3,4-dihydroxyphenyl)propanoate mesylate may be administered to a patient in a therapeutically effective amount. It will be understood, however, that the amount of (2R)-2-phenylcarbonyloxypropyl (2S)-2-amino-3-(3,4-dihydroxyphenyl)propanoate mesylate actually administered will be determined by a physician, in the light of the relevant circumstances, including the condition to be treated, the chosen route of administration, the actual compound administered, the age, weight, and response of the individual patient, the disease being treated, the severity of the patient's symptoms, and the like.

For preparing solid compositions such as tablets, (2R)-2-phenylcarbonyloxypropyl (2S)-2-amino-3-(3,4-dihydroxyphenyl)propanoate mesylate may be mixed with a pharmaceutical excipient, diluent, carrier and/or adjuvant to form a solid pre-formulation composition containing a homogeneous mixture containing (2R)-2-phenylcarbonyloxypropyl (2S)-2-amino-3-(3,4-dihydroxyphenyl)propanoate mesylate. When referring to these pre-formulation compositions as homogeneous, it is meant that (2R)-2-phenylcarbonyloxypropyl (2S)-2-amino-3-(3,4-dihydroxyphenyl)propanoate mesylate is dispersed evenly throughout the composition so that the composition can be readily subdivided into equally effective unit dosage forms such as tablets, pills, or capsules. This solid pre-formulation can then be subdivided into unit dosage forms of the type described herein comprising, for example, an equivalent weight of levodopa ranging from about 10 mg to about 10 g.

Tablets or pills comprising (2R)-2-phenylcarbonyloxypropyl (2S)-2-amino-3-(3,4-dihydroxyphenyl)propanoate mesylate may be coated or otherwise compounded to provide a dosage form affording the advantage of sustained release. For example, a tablet or pill may comprise an inner dosage and an outer dosage component, the latter being in the form of an envelope over and/or enclosing the former. The two components may be separated by an enteric layer. The enteric layer may serve to resist disintegration in the stomach and permit the inner component to pass intact into the duodenum, or to delay release. A variety of materials may be used for such enteric layers or coatings. For example, such materials include a number of polymeric acids and mixtures of polymeric acids with such materials as shellac, cetyl alcohol, or cellulose acetate.

Liquid dosage forms in which the compositions (2R)-2-phenylcarbonyloxypropyl (2S)-2-amino-3-(3,4-dihydroxyphenyl)propanoate mesylate may be incorporated for oral administration or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Sustained Release Oral Dosage Forms (2R)-2-Phenylcarbonyloxypropyl (2S)-2-amino-3-(3,4-dihydroxyphenyl)propanoate mesylate may be practiced with a number of different dosage forms, which can be adapted to provide sustained release of (2R)-2-phenylcarbonyloxypropyl (2S)-2-amino-3-(3,4-dihydroxyphenyl)propanoate mesylate upon oral administration.

In certain embodiments, a sustained release oral dosage form can comprise beads that on dissolution or diffusion release the prodrug over an extended period of hours, in certain embodiments, over a period of at least about 4 hours, in some embodiments, over a period of at least about 8 hours, over a period of at least about 12 hours, over a period of at least about 16 hours, over a period of at least about 20 hours, over a period of at least about 24 hours, and in certain embodiments, over a period of more than about 24 hours. Prodrug-releasing beads may have a central composition or core comprising (2R)-2-phenylcarbonyloxypropyl (2S)-2-amino-3-(3,4-dihydroxyphenyl)propanoate mesylate and at least one pharmaceutically acceptable vehicle, and may include an optional lubricant, antioxidant, and/or buffer. Examples of suitable timed-release beads are disclosed, for example, in Lu, *Int. J. Pharm.* 1994, 112, 117-124; "Remington's Pharmaceutical Sciences," 21st Edition, Lippincott Williams & Wilcox, (2005); Fincher, *J. Pharm. Sci.* 1968, 57, 1825-1835; and U.S. Pat. No. 4,083,949). Examples of suitable sustained release tablets are disclosed, for example, in "Remington's Pharmaceutical Sciences," 21st Edition, Lippincott Williams & Wilcox, (2005). In certain embodiments, an oral sustained release pump may be used (see Langer, *Science* 1990, 249, 1527-1533; Sefton, *CRC Crit. Ref Biomed. Eng.* 1987, 14, 201; and Saudek et al., *N. Engl. J. Med.* 1989, 321, 574).

In certain embodiments, polymeric materials may be used for oral sustained release delivery such as described, for example, in "Medical Applications of Controlled Release," Langer and Wise (eds.), CRC Press, Boca Raton, Fla. (1974); "Controlled Drug Bioavailability, Drug Product Design and Performance," Smolen and Ball (eds.), Wiley, New York (1984); Ranger and Peppas, *J. Macromol. Sci. Rev. Macromol Chem* 1983, 23, 61; Levy et al., *Science* 1985, 228, 190; During et al., *Ann. Neurol* 1989, 25, 351; and Howard et al., *J. Neurosurg* 1989, 71, 105.

In certain embodiments, enteric-coated preparations may be used for oral sustained release administration. In certain embodiments, coating materials include polymers with a pH-dependent solubility (i.e., pH-controlled release), polymers with a slow or pH-dependent rate of swelling, dissolution or erosion (i.e., time-controlled release), polymers that can be degraded by enzymes (i.e., enzyme-controlled release) and polymers that form firm layers that can be destroyed by an increase in pressure (i.e., pressure-controlled release).

In certain embodiments, drug-releasing lipid matrices or prodrug-releasing waxes may be used for oral sustained release administration.

In certain embodiments, controlled-release systems may be placed in proximity to the target of (2R)-2-phenylcarbonyloxypropyl (2S)-2-amino-3-(3,4-dihydroxyphenyl)propanoate mesylate or levodopa metabolite, thus requiring only a fraction of the systemic dose (see Goodson, in "Medical Applications of Controlled Release," vol. 2, 115-138 (1984)). Other controlled-release systems discussed in Langer, *Science* 1990, 249, 1527-1533, may also be used.

In certain embodiments, dosage forms may comprise (2R)-2-phenylcarbonyloxypropyl (2S)-2-amino-3-(3,4-dihydroxyphenyl)propanoate mesylate coated on a polymer substrate. The polymer may be an erodible or a non-erodible polymer. Representative biodegradable polymers are described, for example, in Rosoff, "Controlled Release of Drugs," Chap. 2, 53-95 (1989); and U.S. Pat. Nos. 3,811,444; 3,962,414; 4,066,747; 4,070,347; 4,079,038; and 4,093,709.

In certain embodiments, a dosage form may comprise (2R)-2-phenylcarbonyloxypropyl (2S)-2-amino-3-(3,4-dihydroxyphenyl)propanoate mesylate loaded into a polymer that releases the prodrug by diffusion through a polymer, or by flux through pores or by rupture of a polymer matrix as described, for example, in Coleman et al., *Polymers* 1990, 31, 1187-1231; Roerdink et al., *Drug Carrier Systems* 1989, 9, 57-100; Leong et al., *Adv. Drug Delivery Rev.* 1987, 1, 199-233; Roff et al., "Handbook of Common Polymers," 1971, CRC Press; and U.S. Pat. No. 3,992,518.

In certain embodiments, osmotic delivery systems are used for oral sustained release administration (Verma et al., *Drug Dev. Ind. Pharm.* 2000, 26, 695-708). In certain embodiments, OROS™ osmotic devices are used for oral sustained release delivery devices (Theeuwes et al., U.S. Pat. No. 3,845,770; Theeuwes et al., U.S. Pat. No. 3,916,899).

Regardless of the specific form of sustained release oral dosage form used, (2R)-2-phenylcarbonyloxypropyl (2S)-2-amino-3-(3,4-dihydroxyphenyl)propanoate mesylate may be released from a dosage form such as an orally administered dosage form, over a sufficient period of time to provide prolonged therapeutic concentrations of levodopa in the blood of a patient enabling administration of the dosage form on only a once or twice per day basis. Following oral administration, dosage forms comprising (2R)-2-phenylcarbonyloxypropyl (2S)-2-amino-3-(3,4-dihydroxyphenyl)propanoate mesylate can provide a therapeutic or prophylactic concentration of levodopa in the plasma and/or blood of a patient for a time period of at least about 4 hours, in certain embodiments, for at least about 8 hours, for at least about 12 hours, for at least about 16 hours, for at least about 20 hours, and in certain embodiments, for at least about 24 hours following oral administration of the dosage form to the patient. A therapeutically or prophylactically effective concentration of levodopa in the blood and/or plasma of a patient can depend on a number of factors including, for example, the disease being treated, the severity of the disease, the weight of the patient, the health of the patient, and so forth.

Pharmaceutical compositions provided by the present disclosure may be administered for therapeutic or prophylactic treatments. A therapeutic amount is an amount sufficient to remedy a disease state or symptoms, or otherwise prevent, hinder, retard, or reverse the progression of disease or any other undesirable symptoms in any way whatsoever. In prophylactic applications, pharmaceutical compositions or the present disclosure may be administered to a patient susceptible to or otherwise at risk of a particular disease or infection. Hence, a prophylactically effective amount is an amount sufficient to prevent, hinder or retard a disease state or its symptoms.

An appropriate dosage of the pharmaceutical composition may be determined according to any one of several well-established protocols. For example, animal studies, such as studies using mice or rats, may be used to determine an appropriate dose of a pharmaceutical compound. The results from animal studies can be extrapolated to determine doses for use in other species, such as for example, humans. For example, the efficacy of (2R)-2-phenylcarbonyloxypropyl (2S)-2-amino-3-(3,4-dihydroxyphenyl)propanoate mesylate and compositions thereof for treating Parkinson's disease may be assessed using animal and human models of Parkinson's disease and clinical studies. Animal and human models of Parkinson's disease are known (see, e.g., O'Neil et al., *CNS Drug Rev.* 2005, 11(1), 77-96; Faulkner et al., *Ann. Pharmacother.* 2003, 37(2), 282-6; Olson et al., *Am. J. Med.* 1997, 102(1), 60-6; Van Blercom et al., *Clin Neuropharmacol.* 2004, 27(3), 124-8; Cho et al., *Biochem. Biophys. Res. Commun.* 2006, 341, 6-12; Emborg, *J. Neuro. Meth.* 2004, 139, 121-143; Tolwani et al., *Lab Anim Sci* 1999, 49(4), 363-71; Hirsch et al., *J Neural Transm Suppl* 2003, 65, 89-100; Orth and Tabrizi, *Mov Disord* 2003, 18(7), 729-37; and Betarbet et al., *Bioessays* 2002, 24(4), 308-18).

(2R)-2-Phenylcarbonyloxypropyl (2S)-2-amino-3-(3,4-dihydroxyphenyl)propanoate mesylate or pharmaceutical compositions thereof may be administered as sustained release systems, and in certain embodiments, as orally administered sustained release systems. In certain embodiments, the compounds may be delivered by oral sustained release administration. In certain embodiments, (2R)-2-phenylcarbonyloxypropyl (2S)-2-amino-3-(3,4-dihydroxyphenyl)propanoate mesylate or pharmaceutical compositions thereof may be administered twice per day, in certain embodiments, once per day, and in certain embodiments at intervals greater than once per day.

Combination Therapy

In certain embodiments, (2R)-2-phenylcarbonyloxypropyl (2S)-2-amino-3-(3,4-dihydroxyphenyl)propanoate mesylate or crystalline form thereof may be used in combination therapy with at least one other therapeutic agent. Pharmaceutical compositions provided by the present disclosure may include, in addition to (2R)-2-phenylcarbonyloxypropyl (2S)-2-amino-3-(3,4-dihydroxyphenyl)propanoate mesylate, one or more therapeutic agents effective for treating the same or different disease, disorder, or condition.

Methods provided by the present disclosure include administration of (2R)-2-phenylcarbonyloxypropyl (2S)-2-amino-3-(3,4-dihydroxyphenyl)propanoate mesylate or pharmaceutical compositions thereof and one or more other therapeutic agents, provided that the combined administration does not inhibit the therapeutic efficacy of (2R)-2-phenylcarbonyloxypropyl (2S)-2-amino-3-(3,4-dihydroxyphenyl)propanoate mesylate or levodopa and/or does not produce adverse combination effects.

(2R)-2-Phenylcarbonyloxypropyl (2S)-2-amino-3-(3,4-dihydroxyphenyl)propanoate mesylate and another therapeutic agent or agents may act additively or synergistically. In certain embodiments, pharmaceutical compositions provided by the present disclosure can be administered concurrently with the administration of another therapeutic agent, which may be contained in the same pharmaceutical composition as, or in a different composition from that containing (2R)-2-phenylcarbonyloxypropyl (2S)-2-amino-3-(3,4-dihydroxyphenyl)propanoate mesylate. In certain embodiments, (2R)-2-phenylcarbonyloxypropyl (2S)-2-amino-3-(3,4-dihydroxyphenyl)propanoate mesylate may be administered prior or subsequent to administration of another therapeutic agent. In certain embodiments of combination therapy, the combination therapy can comprise alternating between administering a composition provided by the present disclosure and a composition comprising another therapeutic agent, e.g., to minimize adverse side effects associated with a particular drug. When (2R)-2-phenylcarbonyloxypropyl (2S)-2-amino-3-(3,4-dihydroxyphenyl)propanoate mesylate or crystalline form thereof is administered concurrently with another therapeutic agent that can potentially produce adverse side effects including, but not limited to, toxicity, the therapeutic agent may advantageously be administered at a dose that falls below the threshold at which the adverse side effect is elicited.

In certain embodiments, (2R)-2-phenylcarbonyloxypropyl (2S)-2-amino-3-(3,4-dihydroxyphenyl)propanoate mesylate may further be administered together with one or more compounds that enhance, modulate, and/or control the release, bioavailability, therapeutic efficacy, therapeutic potency, and/or stability of (2R)-2-phenylcarbonyloxypropyl (2S)-2-amino-3-(3,4-dihydroxyphenyl)propanoate mesylate or crystalline form thereof and/or levodopa. For example, to enhance therapeutic efficacy the levodopa prodrug mesylate may be co-administered with one or more active agents to increase the absorption or diffusion of (2R)-2-phenylcarbonyloxypropyl (2S)-2-amino-3-(3,4-dihydroxyphenyl)propanoate mesylate or crystalline form thereof and/or levodopa through the gastrointestinal tract, or to modify degradation of the (2R)-2-phenylcarbonyloxypropyl (2S)-2-amino-3-(3,4-dihydroxyphenyl)propanoate mesylate or crystalline form thereof and/or levodopa in the systemic circulation. In certain embodiments, (2R)-2-phenylcarbonyloxypropyl (2S)-2-amino-3-(3,4-dihydroxyphenyl)propanoate mesylate may be co-administered with an active agent having pharmacological effects that enhance the therapeutic efficacy of levodopa after being released from (2R)-2-phenylcarbonyloxypropyl (2S)-2-amino-3-(3,4-dihydroxyphenyl)propanoate mesylate or crystalline form thereof. In certain embodiments, (2R)-2-phenylcarbonyloxypropyl (2S)-2-amino-3-(3,4-dihydroxyphenyl)propanoate mesylate may be co-administered with an active agent having pharmacological effects that enhance the therapeutic efficacy of dopamine after being released from levodopa.

In certain embodiments, (2R)-2-phenylcarbonyloxypropyl (2S)-2-amino-3-(3,4-dihydroxyphenyl)propanoate mesylate or crystalline form thereof or pharmaceutical compositions comprising (2R)-2-phenylcarbonyloxypropyl (2S)-2-amino-3-(3,4-dihydroxyphenyl)propanoate mesylate or crystalline form thereof may be administered to a patient together with another compound for treating Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, or excessive daytime sleepiness.

Examples of drugs useful for treating Parkinson's disease include amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergolide, piribedil, pramipexole, propentofylline, rasagiline, remacemide, ropinirole, selegiline, spheramine, terguride, entacapone, and tolcapone.

Examples of drugs useful for treating mood disorders such as depression include tricyclic antidepressants such as amitriptyline, amoxapine, clomipramine, desipramine, doxepin, imipramine, maprotiline, nortriptyline, protriptyline, and trimipramine; selective serotonin reuptake inhibitors such as citalopram, escitalopram, fluoxetine, fluvoxamine, paroxetine, and sertraline; serotonin-noradrenaline reuptake inhibitors such as venlafaxine, duloxetine, sibutramine, and milnacipran; monoamine oxidase inhibitors such as phenelzine and tranylcypromine; and psychostimulants such as dextroamphetamine and methylphenidate. Other antidepressants include benmoxine, butriptyline, dosulepin, imipramine, kitanserin, lofepramine, medifoxamine, mianserin, mirtazapine, viloxazine, cotinine, nisoxetine, reboxetine, tianeptine, acetaphenazine, binedaline, brofaromine, cericlamine, clovoxamine, iproniazid, isocarboxazid, moclobemide, phenyhydrazine, selegiline, sibutramine, ademetionine, adrafinil, amesergide, amisulpride, amperozide, benactyzine, bupropion, caroxazone, gepirone, idazoxan, metralindole, minaprine, nefazodone, nomifensine, ritanserin, roxindole, S-adenosylmethionine, escitalopram, tofenacin, trazodone, tryptophan, zalospirone, and Saint John's wort. (2R)-2-Phenylcarbonyloxypropyl (2S)-2-amino-3-(3,4-dihydroxyphenyl)propanoate mesylate or crystalline form thereof and pharmaceutical compositions thereof may also be used in conjunction with psychotherapy or electroconvulsive therapy to treat mood disorders such as depression.

Examples of drugs useful for treating attention deficit disorder include atomoxetine, bupropion, dexmethylphenidate, dextroamphetamine, metamphetamine, methylphenidate, and pemoline.

Examples of drugs for treating schizophrenia include aripiprazole, loxapine, mesoridazine, quetiapine, reserpine, thioridazine, trifluoperazine, and ziprasidone.

Examples of drugs useful for treating manic depression include carbamazepine, clonazepam, clonidine, valproic acid, verapamil, lamotrigine, gabapentin, topiramate, lithium, clozapine, olanzapine, risperidone, quetiapine, ziprasidone, clonazepam, lorazepam, zolipidem, St. John's wort, and omega-3 fatty acids.

Examples of drugs useful for treating cognitive or memory disorders include antipsychotic drugs such as chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, and ziprasidone; sedatives such as diazepam and lorazepam; benzodiazepines such as alprazolam, chlordiazepoxide, clonazepam, clorazepate, diazepam, lorazepam, and oxazepam; nonsteroidal anti-inflammatory drugs such as aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib; acetylcholinesterase inhibitors such as donepezil, galantamine, rivastigmine, physostigmine, and tacrine; and N-methyl-D-aspartate (NMDA) receptor blockers such as memantine.

Examples of drugs useful for treating restless legs syndrome include dopaminergics such as levodopa, pergolide mesylate, pramipexole, and rinirole hydrochloride, benzodiazepines such as clonazepam and diazepam, opioids such as codeine, propoxyphene, and oxycodone, and anticonvulsants such as gabapentin and carbamazepine.

Examples of drugs useful for treating movement disorders such as tardive dyskinesia include reserpine, tetrabenazine, and vitamin E.

Examples of drugs useful for treating Huntington's disease include antipsychotics such as haloperidol, chlorpromazine, and olanzapine; antidepressants such as fluoxetine, sertraline hydrochloride, and nortriptyline; tranquilizers such as benzodiazepines, paroxetine, venlafaxin, and beta-blockers; mood-stabilizers such as lithium, valproate, and carbamazepine; and *Botulinum* toxin.

Examples of drugs useful for treating Tourette's syndrome include haloperidol, pergolide, and pimozide.

Examples of drugs useful for treating hypertension include acebutolol, amiloride, amlodipine, atenolol, benazepril, betaxolol, bisoprolol, candesartan captopril, careolol, carvedilol, chlorothiazide, chlorthalidone, clonidine, diltiazem, doxazosin, enalapril, eplerenone, eprosartan, felodipine, fosinopril, furosemide, guanabenz, guanethidine, guanfacine, hydralazine, hydrochlorothiazide, indapamide, irbesartan, isradipine, labetalol, lisinopril, losartan, methyldopa, metolazone, metoprolol, minoxidil, moexipril, nadolol, nicardipine, nifedipine, nisoldipine, nitroglycerin, olmesartan, perindopril, pindolol, prazosin, propranolol, quinapril, ramipril, reserpine, spironolactone, telmisartan, terazosin, timolol, torsemide, trandolapril, valsartan, and verapamil.

Examples of drugs useful for treating alcohol addiction or abuse include disulfiram, naltrexone, clonidine, methadone, 1-α-acetylmethadol, buprenorphine, and bupropion.

Examples of drugs useful for treating narcotic addiction or abuse include buprenorphine, tramadol, methadone, and naltrexone.

Examples of drugs useful for treating nicotine addiction or abuse include bupropion, clonidine, and nicotine.

Examples of drugs useful for treating congestive heart failure include alllopurinol, amiloride, amlodipine, benazepril, bisoprolol, carvedilol, digoxin, enalapril, eplerenone, fosinopril, furosemide, hydrochlorothiazide, hydralazine, isosorbide dinitrate, isosorbide mononitrate, lisinopril, metoprolol, moexipril, nesiritide, nicardipine, nifedipine, nitroglycerin, perindopril, prazosin, quinapril, ramipril, spironolactone, torsemide, trandolapril, triamcinolone, and valsartan.

Examples of drugs useful for treating excessive daytime sleepiness include dextroamphetamine, methylphenidate, modafinil, and sodium oxybate.

EXAMPLES

The following examples describe in detail preparation of (2R)-2-phenylcarbonyloxypropyl (2S)-2-amino-3-(3,4-dihydroxyphenyl)propanoate mesylate and crystalline form thereof, pharmaceutical compositions thereof, and uses thereof. It will be apparent to one skilled in the art that many modifications, both to materials and methods, may be practiced without departing from the scope of the disclosure. Example 7 is prophetic.

In the examples, the following abbreviations have the following meanings. If an abbreviation is not defined, it has its generally accepted meaning.

ACN=acetonitrile

| | |
|---|---|
| DCM = | dichloromethane |
| EtOAc = | ethylacetate |
| eq = | equivalents |
| g = | gram |
| h = | hour |
| J = | Joules |
| kg = | kilogram |
| kV = | kilovolt |
| LC/MS = | liquid chromatography/mass spectroscopy |
| MeOH = | methanol |
| min = | minute |
| mA = | milliamp |
| mg = | milligram |
| mL = | milliliter |
| mm = | millimeter |
| mmol = | millimoles |
| MTBE = | methyl tert-butyl ether |
| µg = | microgram |
| µL = | microliter |

Example 1

(2R)-2-Phenylcarbonyloxypropyl (2S)-2-(tert-Butoxycarbonyl)amino-3-(3,4-dihydroxyphenyl)propanoate (2)

Step A: (2S)-3-(3,4-Dihydroxyphenyl)-2-[(tert-butoxycarbonyl)amino]propanoic Acid, Tetrabutylammonium Salt A solution of N-Boc-(L)-Dopa (175 g, 0.59 mol) in methanol (1 L) was cautiously mixed with a methanolic solution of tetrabutylammonium hydroxide (1.0 M, 0.55 L) at 0° C. for 30 min. The mixture was then concentrated under reduced pressure and dried by azeotroping with toluene twice. The residue was crystallized after cooling at 4° C. for 16 h. The resulting crystalline solid was washed with acetone (400 mL×3), collected on a Buchner funnel, and then dried under high vacuum to afford 245 g (83% yield) of the title compound. $^1$H NMR (400 MHz, DMSO-$d_6$): δ 0.94 (t, J=7.6 Hz, 12H), 1.30 (m, 17H), 1.60 (m, 8H), 3.18 (m, 8H), 4.58 (m, 1H), 5.68 (d, J=5.6 Hz, 1H), 6.30 (d, J=7.6 Hz, 1H), 6.46 (d, J=8.0 Hz, 1H), 6.51 (s, 1H), 8.85 (s, 1H); 8.94 (s, 1H).

Step B: (1R)-2-Bromo-1-methylethyl Benzoate

A solution of (2R)-propylene glycol (20.0 g, 262.8 mmol), benzaldehyde (33.4 mL, 328.6 mmol, 1.25 eq) and p-toluenesulfonic acid (2.5 g, 0.05 eq) in benzene (200 mL) was refluxed for 8 h with removal of water via a Dean-Stark apparatus. The cooled solution was diluted with diethyl ether (100 mL), washed with aqueous NaOH (15%, 100 mL), brined (100 mL) and dried over $Na_2SO_4$. After filtration; removal of solvent under reduced pressure gave 44 g of crude benzaldehyde (2R)-propylene glycolacetal as an oil.

To a solution of the above crude benzaldehyde (2R)-propylene glycolacetal (10.0 g, 60.9 mmol) in hexane (100 mL) was added N-bromosuccinamide (NBS) (11.9 g, 67 mmol, 1.1 eq). The resulting mixture was stirred at room temperature overnight. The suspension was filtered through Celite and the filtrate was diluted with hexane (300 mL), washed with saturated $NaHCO_3$ (100 mL), brined (100 mL), and dried over $Na_2SO_4$. After filtration, removal of the solvent under reduced pressure gave the title compound (quantitative yield) as an oil. $^1$H NMR (400 MHz, $CDCl_3$): δ 1.48 (d, J=6.4 Hz, 3H), 3.58 (m, 2H), 5.31 (m, 1H), 7.43 (t, J=7.6 Hz, 2H), 7.53 (t, J=7.6 Hz, 1H), 8.05 (d, J=7.2 Hz, 2H).

Step C: (2R)-2-Phenylcarbonyloxypropyl (2S)-2-(tert-Butoxycarbonyl)amino-3-(3,4-dihydroxyphenyl)propanoate (2)

A suspension of (1R)-2-bromo-1-methylethyl benzoate (4.98 g, 20.6 mmol), N-Boc-L-DOPA-COOH (7.3 g, 25 mmol), and cesium bicarbonate (4.85 g, 25 mmol) in N,N-dimethylacetamide (100 mL) was stirred at 55° C. for 16 h. The solvent was evaporated under vacuum. Ethyl acetate was added to the residue and the resulting solution was washed with water, then 5% $NaHCO_3$, brine, and dried over $Na_2SO_4$. After removing the solvent under reduced pressure, chromatography (silica gel, 30% ethyl acetate in hexane) of the residue gave 6.3 g (68% yield) of the title compound 2 as a white solid. $^1$H NMR (400 MHz, $CD_3OD$): δ 1.25 (s, 9H), 1.40 (d, J=6.4 Hz, 3H), 2.99 (dd, J=7.6, 14.4 Hz, 1H), 3.10 (dd, J=5.6, 14.4 Hz, 1H), 4.24 (dd, J=5.6, 7.4 Hz, 1H), 4.38 (dd, J=6.8, 11.6 Hz, 1H), 4.52 (dd, J=3.2, 11.6 Hz, 1H), 5.40 (m, 1H), 6.53 (dd, J=2.2, 8.4 Hz, 1H), 6.66 (d, J=2.2 Hz, 1H), 6.69 (d, J=8.4 Hz, 1H), 7.47 (t, J=7.6 Hz, 2H), 7.60 (t, J=7.6 Hz, 1H), 8.02 (d, J=7.6 Hz, 2H). MS (ESI) m/z 360.15 $(M+H)^+$ and 358.09 $(M-H)^-$.

Example 2

(2R)-2-Phenylcarbonyloxypropyl (2S)-2-Amino-3-(3,4-dihydroxyphenyl)propanoate Mesylate (1)

Method 1:

Step A: (2R)-2-Phenylcarbonyloxypropyl (2S)-2-Amino-3-(3,4-dihydroxyphenyl)propanoate Hydrochloride (3)

A solution of (2R)-2-phenylcarbonyloxypropyl (2S)-2-(tert-butoxycarbonyl)amino-3-(3,4-dihydroxyphenyl)propanoate 2 (6.3 g, 13.7 mmol) in 50 mL of 4N HCl in dioxane was stirred at room temperature for 30 min. The reaction mixture was concentrated to dryness under reduced pressure. The resulting residue was dissolved in about 20 mL of anhydrous acetonitrile and 4 mL of ether. The solution was refrigerated, and the resulting white precipitate was filtered, washed with ether, and dried under vacuum to afford 4.7 g (87% yield) of the hydrochloride salt 3 as a white solid. NMR (400 MHz, $CD_3OD$): δ 1.40 (d, J=6.4 Hz, 3H), 2.99 (dd, J=7.6, 14.4 Hz, 1H), 3.10 (dd, J=5.6, 14.4 Hz, 1H), 4.24 (dd, J=6, 8 Hz, 1H), 4.38 (dd, J=6.8, 11.6 Hz, 1H), 4.52 (dd, J=3.2, 11.6 Hz, 1H), 5.40 (m, 1H), 6.52 (dd, J=2.2, 8.4 Hz, 1H), 6.66 (d, J=2.2 Hz, 1H), 6.69 (d, J=8.2 Hz, 1H), 7.47 (t, J=7.6 Hz, 2H), 7.60 (t, J=7.6 Hz, 1H), 8.02 (d, J=7.6 Hz, 2H). MS (ESI) m/z 360.15 $(M+H)^+$ and 358.09 $(M-H)^-$.

Step B: (2R)-2-Phenylcarbonyloxypropyl (2S)-2-Amino-3-(3,4-dihydroxyphenyl)propanoate Mesylate (1)

A solution of $NaHCO_3$ (9.87 g, 117.5 mmol) in water (80 mL) was slowly added to a solution of the hydrochloride salt 3 (31.0 g, 78.3 mmol) in water (300 mL). The resulting aqueous suspension was extracted with EtOAc (2×400 mL). The combined EtOAc extract was washed with water, then brine, and dried through $MgSO_4$. Methanesulfonic acid (6.04 mL, 93.12 mmol) was slowly added to the EtOAc solution while stirred. White precipitate formed as soon as the addition of methanesulfonic acid was complete. The suspension was stirred for another 30 min and then filtered. The filter cake was washed three times with EtOAc and vacuum dried overnight to afford 35.4 g (quantitative) of the mesylate salt 1 as a white solid. $^1$H NMR (400 MHz, $CD_3OD$): δ 1.40 (d, J=6.4 Hz, 3H), 2.70 (s, 3H), 2.98 (dd, J=7.8, 14.6 Hz, 1H), 3.10 (dd, J=5.6, 14.4 Hz, 1H), 4.24 (dd, J=5.8, 7.8 Hz, 1H), 4.38 (dd, J=6.8, 12.0 Hz, 1H), 4.52 (dd, J=3.4, 11.8 Hz, 1H), 5.40 (dp, J=3.2, 6.4 Hz, 1H), 6.52 (dd, J=2.2, 8.2 Hz, 1H), 6.67 (d, J=2.2 Hz, 1H), 6.69 (d, J=8.0 Hz, 1H), 7.47 (t, J=7.6 Hz, 2H), 7.60 (br t, J=7.4 Hz, 1H), 8.01 (d, J=7.6 Hz, 2H). MS (ESI) m/z 360.07 $(M+H)^+$ and 358.01 $(M-H)^-$.

Method 2:

Methanesulfonic acid (3.9 mL, 60.1 mmol) was slowly added to a solution of (2R)-2-phenylcarbonyloxypropyl (2S)-2-(tert-butoxycarbonyl)amino-3-(3,4-dihydroxyphenyl)propanoate 2 (11.0 g, 22.1 mmol) in 1,4-dioxane (30 mL) while stirred at room temperature. The reaction mixture was stirred for 2 h. The solution was slowly added to methyl tert-butyl ether (MTBE) (600 mL) with vigorous stirring. The resulting suspension was filtered. The filter cake was washed three times with methyl tert-butyl ether and air dried to afford 5.48 g (54% yield) of the mesylate salt 1 as an off-white solid.

Method 3:

A solution of (2R)-2-phenylcarbonyloxypropyl (2S)-2-(tert-butoxycarbonyl)amino-3-(3,4-dihydroxyphenyl)propanoate 2 (10.5 g, 21.1 mmol) in 34 mL (6.0 eq) of 4.0 N HCl/1,4-dioxane was stirred at room temperature for 1 h. Methanesulfonic acid (1.48 mL, 22.8 mmol) was slowly added to the reaction mixture while stirred at room temperature. The solution was concentrated under vacuum to afford the mesylate salt 1 as a brown solid.

Example 3

Preparation of Crystalline (2R)-2-Phenylcarbonyloxypropyl (2S)-2-Amino-3-(3,4-dihydroxyphenyl)propanoate Mesylate (1)

The mesylate salt 1 (10.0 g, 22.0 mmol) was dissolved in 200 mL of isopropanol at 70° C. and the resulting solution was cooled to room temperature. Filtration afforded 5.8 g (58% yield) of the crystalline mesylate salt 1 as a white crystalline solid. (m.p. 160.5-161.3° C.).

Crystallization of the mesylate salt 1 was carried out in various single component or mixed component solvents including those listed in Table 1. Differential scanning calorimetry (DSC) was used to evaluate the number of crystalline forms of the mesylate salt 1 produced by the various solvents.

A DSC thermogram of the crystalline mesylate salt 1 obtained by crystallization in isopropanol is shown in FIG. 1.

DSC analysis of the crystalline mesylate salt 1 crystallized from each solvent listed in Table 1 showed an endothermic event represented by a single, sharp peak at 165.8±1.1° C. (scan rate 10° C./min or 15° C./min). Table 1 shows examples of solvents used for crystallization of the mesylate salt 1 and the corresponding DSC parameters, endothermic temperature (° C.) and ΔH (J/g).

TABLE 1

| Solvent | Endothermic Temperature (° C.) | ΔH (J/g) |
|---|---|---|
| 1% $H_2O$ in ACN | 166.8 | 89.9 |
| 3% $H_2O$ in ACN | 165.4 | 84.5 |
| 1% $H_2O$ in Isopropanol, | 165.1 | 91.5 |
| Isopropanol | 165.8 | 90.2 |
| MeOH/MTBE (1:7) | 166.9 | 92.3 |
| MeOH/MTBE (1:6) | 164.9 | 90.4 |
| MeOH/MTBE (1:5) | 166.0 | 97.2 |
| 0.5% $H_2O$ in MeOH/MTBE (1:5) | 165.1 | 98.3 |
| Dioxane | 165.2 | 87.9 |
| Acetone | 165.3 | 90.0 |
| 3% $H_2O$ in EtOAc | 166.8 | 115.9 |
| 2% $H_2O$ in Acetone/MTBE (5:3) | 165.8 | 90.1 |
| 0.75% $H_2O$ in Acetone/ACN (1:1) | 165.7 | 90.9 |
| 2.5% $H_2O$ in EtOAc | 165.8 | 90.1 |
| EtOH/EtOAc (1:3) | 165.3 | 94.5 |
| EtOH/Hexane (1:1) | 164.8 | 78.0 |

Example 4

Synthesis and Crystallization of (2R)-2-Phenylcarbonyloxypropyl (2S)-2-Amino-3-(3,4-dihydroxyphenyl)propanoate Mesylate (1)

To an aqueous solution of the hydrochloride salt 3 (65.0 g, 164 mmol, 200 mL) was added aqueous $NaHCO_3$ solution (20.7 g, 246 mmol, 200 mL) and then extracted with EtOAc (2×400 mL). The pooled organic extracts were washed with brine and dried over $Na_2SO_4$. After filtration, methanesulfonic acid (12.8 mL, 197 mmol) was slowly added to the filtrate while stirring at room temperature. The resulting white crystals were filtered through a fritted funnel, washed with EtOAc (3×1000 mL) and dried under high vacuum at 50° C. to afford 73.6 g (98.4% yield) of the mesylate salt 1. $^1$H NMR (400 MHz, $CD_3OD$): δ 1.40 (d, J=6.4 Hz, 3H), 2.70 (s, 3H), 2.98 (dd, J=7.8, 14.6 Hz, 1H), 3.10 (dd, J=5.6, 14.4 Hz, 1H), 4.24 (dd, J=5.8, 7.8 Hz, 1H), 4.38 (dd, J=6.8, 12.0 Hz, 1H), 4.52 (dd, J=3.4, 11.8 Hz, 1H), 5.40 (dp, J=3.2, 6.4 Hz, 1H), 6.52 (dd, J=2.2, 8.2 Hz, 1H), 6.67 (d, J=2.2 Hz, 1H), 6.69 (d, J=8.0 Hz, 1H), 7.47 (t, J=7.6' Hz, 2H), 7.60 (br t, J=7.4 Hz, 1H), 8.01 (d, J=7.6 Hz, 2H). MS (ESI) m/z 360.07 $(M+H)^+$ and 358.01 $(M-H)^-$.

Example 5

X-Ray Powder Diffraction (XRPD) Analysis of Crystalline (2R)-2-Phenylcarbonyloxypropyl (2S)-2-Amino-3-(3,4-dihydroxyphenyl)propanoate Mesylate (1)

XRPD analyses were performed using a Shimadzu XRD-6000 X-ray power diffractometer with Cu Kα radiation. The instrument was equipped with a long fine focus X-ray tube. The tube voltage and current were set to 40 kV and 40 mA, respectively. The divergence and scattering slits were set at 1° and the receiving slit was set at 0.15 mm. Diffracted radiation was detected using a NaI scintillation detector. A θ-2θ continuous scan at 3°/min (0.4 sec/0.02° step) from 2.5 to 40°2θ was used. Instrument alignment was checked by analyzing a silicon standard. Data were collected and analyzed using XRD-6000 v.4.1 software. Five representative diffraction patterns of crystalline mesylate salt 1 crystallized from 1% $H_2O$ in isopropanol, isopropanol, MeOH/MTBE (1:7), 0.5% $H_2O$ in MeOH/MTBE (1:5), and 1% $H_2O$ in acetonitrile are shown in FIGS. 2-6, respectively. The presence of clearly resolved peaks at similar diffraction angles confirms that the same crystalline form of the mesylate salt 1 was produced upon crystallination from these solvents.

Example 6

Uptake of Levodopa Prodrugs Following Administration of Levodopa Prodrugs and Carbidopa in Rats Sustained release oral dosage forms, which release drug slowly over periods of about 6 to about 24 hours, generally release a significant proportion of the dose within the colon. Thus, drugs suitable for use in such dosage forms should be colonically absorbed. This experiment was conducted to assess the uptake and resultant plasma/blood levels of levodopa, following intracolonic administration of levodopa prodrug mesylate with co-administration of carbidopa (intracolonically, intraperitoneally, or orally), and thereby determine the suitability of levodopa prodrug mesylate for use in an oral sustained release dosage form. Bioavailability of levodopa following co-administration of levodopa prodrug mesylate and carbidopa was calculated relative to oral co-administration of levodopa and carbidopa.

Step A: Administration Protocol

Rats were obtained commercially and were pre-cannulated in the both the ascending colon and the jugular vein. Animals were conscious at the time of the experiment. All animals were fasted overnight and until 4 hours post-dosing of levodopa prodrug. Carbidopa was administered as a solution in water or citrate buffer either orally, intraperitoneally, or intracolonically at a dose equivalent to 25 mg of carbidopa per kg. Either at the same time or 1 hour after carbidopa dosing, levodopa HCl salt or (2R)-2-phenylcarbonyloxypropyl (2S)-2-amino-3-(3,4-dihydroxyphenyl)propanoate mesylate 1 was administered as a solution (in water) directly into the colon via the cannula at a dose equivalent to 75 mg of levodopa per kg. Blood samples (0.3 mL) were obtained from the jugular cannula at intervals over 8 hours and were immediately quenched with sodium metabisulfite to prevent oxidation of levodopa and levodopa prodrug. Blood was then further quenched with methanol/perchloric acid to prevent hydrolysis of the levodopa prodrug. Blood samples were analyzed as described below.

Step B: Sample Preparation for Colonically Absorbed Drug

Methanol/perchloric acid (300 μL) was added to blank 1.5 mL Eppendorf tubes. Rat blood (300 μL) was collected into EDTA tubes containing 75 of sodium metabisulfite at different times and vortexed to mix. A fixed volume of blood (100 μL) was immediately added into the Eppendorf tube and vortexed to mix. Ten microliters of a levodopa standard stock solution (0.04, 0.2, 1, 5, 25, and 100 μg/mL) and 10 μL of the 10% sodium metabisulfite solution was added to 80 μL of blank rat blood to make up a final calibration standard (0.004, 0.02, 0.1, 0.5, 2.5, and 10 μg/mL). Methanol/perchloric acid (300 μL of 50/50) was then added into each tube followed by the addition of 20 μL of p-chlorophenylalanine. The samples were vortexed and centrifuged at 14,000 rpm for 10 min. The supernatant was analyzed by LC/MS/MS.

Step C: LC/MS/IVIES analysis

An API 4000 LC/MS/MS spectrometer equipped with Agilent 1100 binary pumps and a CTC HTS-PAL autosampler were used in the analysis. A Zorbax XDB C8 4.6×150 mm column was used during the analysis. The mobile phases were (A) 0.1% formic acid, and (B) acetonitrile with 0.1% formic acid. The gradient condition was: 5% B for 0.5 min, then to 98% B in 3 min, then maintained at 98% B for 2.5 min. The mobile phase was then returned to 2% B for 2 min. A TurboIonSpray source was used on the API 4000. The analysis was done in positive ion mode and the MRM transition for each analyte was optimized using standard solution. 5 μL of each sample was injected. Non-compartmental analysis was performed using WinNonlin software (v.3.1 Professional Version, Pharsight Corporation, Mountain View, Calif.) on individual animal profiles. Summary statistics on major parameter estimates was performed for $C_{max}$ (peak observed concentration following dosing), $T_{max}$ (time to maximum concentration is the time at which the peak concentration was observed), $AUC_{(0-t)}$ (area under the serum concentration-time curve from time zero to last collection time, estimated using the log-linear trapezoidal method), $AUC_{(0-\infty)}$ (area under the blood concentration time curve from time zero to infinity, estimated using the log-linear trapezoidal method to the last collection time with extrapolation to infinity), and $t_{1/2,z}$ (terminal half-life).

Maximum concentrations of levodopa in the blood ($C_{max}$ values) and the area under blood concentration versus time curve (AUC) values after intracolonic dosing of (2R)-2-phenylcarbonyloxypropyl (2S)-2-amino-3-(3,4-dihydroxyphenyl)propanoate mesylate 1 with carbidopa were significantly higher (>2-fold) than those achieved for colonic administration of levodopa with carbidopa.

Intracolonic co-administration of levodopa and carbidopa results in very low relative bioavailability of levodopa (i.e., only 3% of orally co-administered levodopa and carbidopa). By comparison, co-administration of (2R)-2-phenylcarbonyloxypropyl (2S)-2-amino-3-(3,4-dihydroxyphenyl)propanoate mesylate 1 with carbidopa exhibited improved relative bioavailability of levodopa by at least 2-fold. The data demonstrates that certain levodopa prodrugs can be formulated as compositions suitable for effective sustained oral release and uptake of levodopa prodrug mesylate and/or levodopa from the colon.

Example 7

Use of Crystalline (2R)-2-Phenylcarbonyloxypropyl (2S)-2-Amino-3-(3,4-dihydroxyphenthpropanoate Mesylate (1) for Treating Parkinson's Disease The following clinical study may be used to assess the efficacy of crystalline mesylate salt 1 in treating Parkinson's disease.

Patients with idiopathic PD fulfilling the Queen Square Brain Bank criteria (Gibb et al., *J Neurol Neurosurg Psychiatry* 1988, 51, 745-752) with motor fluctuations and a defined short duration levodopa response (1.5-4 hours) are eligible for inclusion. Clinically relevant peak dose dyskinesias following each morning dose of their current medication are a further pre-requisite. Patients are also required to have been stable on a fixed dose of treatment for a period of at least one month prior to starting the study. Patients are excluded if their current drug regime includes slow-release formulations of levodopa, COMT inhibitors, selegiline, anticholinergic drugs, or other drugs that could potentially interfere with gastric absorption (e.g. antacids). Other exclusion criteria include patients with psychotic symptoms or those on antipsychotic treatment patients with clinically relevant cognitive impairment, defined as MMS (Mini Mental State) score of less than 24 (Folstein et al., *J Psychiatr Res* 1975, 12, 189-198), risk of pregnancy, Hoehn & Yahr stage 5 in off-status, severe, unstable diabetes mellitus, and medical conditions such as unstable cardiovascular disease or moderate to severe renal or hepatic impairment. Full blood count, liver, and renal function blood tests are taken at baseline and after completion of the study.

A randomized, double-blind, and cross-over study design is used. Each patient is randomized to the order in which either LD/DC or one of the two dosages of test compound is administered in a single-dose challenge in double-dummy fashion in three consecutive sessions. Randomization is by computer generation of a treatment number, allocated to each patient according to the order of entry into the study.

Patients are admitted to a hospital for an overnight stay prior to administration of crystalline mesylate salt 1 the next morning on three separate occasions at weekly intervals. After withdrawal of all anti-parkinsonian medication from midnight the previous day crystalline mesylate salt 1 is administered at exactly the same time in the morning in each patient under fasting conditions.

Patients are randomized to the order of the days on which they receive placebo or crystalline mesylate salt 1. The pharmacokinetics of crystalline mesylate salt 1 may be assessed by monitoring plasma levodopa concentration over time. Prior to administration, a 22 G intravenous catheter is inserted in a patient's forearm. Blood samples of 5 ml each are taken at baseline and 15, 30, 45, 60, 75, 90, 105, 120, 140, 160, 180, 210, and 240 minutes after administering crystalline mesylate salt 1 or until a full off-state has been reached if this occurs earlier than 240 minutes after drug ingestion. Samples are centrifuged immediately at the end of each assessment and stored deep frozen until assayed. Plasma levodopa and 3-O-methyl-Dopa levels are assessed by high-pressure liquid chromatography (HPLC). On the last assessment additional blood may be drawn for routine hematology, blood sugar, liver, and renal function.

For clinical assessment, motor function is assessed using UPDRS (United Parkinson's Disease Rating Scale) motor score and BrainTest (Giovanni et al., *J Neurol Neurosurg Psychiatry* 1999, 67, 624-629.), which is a tapping test performed with the patient's more affected hand on the keyboard of a laptop computer. These tests are carried out at baseline and then immediately following each blood sample until patients reach their full on-stage, and thereafter at 3 intervals of 20 min, and 30 min intervals until patients reach their baseline off-status. Once patients reach their full on-state, video recordings are performed three times at 20 min intervals. The following mental and motor tasks, which have been shown to increase dyskinesia (Duriff et al., *Mov Disord* 1999, 14, 242-245) are monitored during each video session: (1) sitting still for 1 minute; (2) performing mental calculations; (3) putting on and buttoning a coat; (4) picking up and drinking from a cup of water; and (5) walking. Videotapes are scored using, for example, versions of the Goetz Rating Scale and the Abnormal Involuntary Movements Scale to document a possible increase in test compound induced dyskinesia.

Actual occurrence and severity of dyskinesia is measured with a Dyskinesia Monitor (Manson et al., *J Neurol Neurosurg Psychiatry* 2000, 68, 196-201). The device is taped to a patient's shoulder on their more affected side. The monitor records during the entire time of a challenging session and provides a measure of the frequency and severity of occurring dyskinesias.

Results can be analyzed using appropriate statistical methods.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A method of treating Parkinson's disease in a patient comprising administering to a patient in need of such treatment a therapeutically effective amount of (2R)-2-phenylcarbonyloxypropyl (2S)-2-amino-3-(3,4-dihydroxyphenyl)propanoate mesylate.

2. The method of claim 1, wherein the (2R)-2-phenylcarbonyloxypropyl (2S)-2-amino-3-(3,4-dihydroxyphenyl)propanoate mesylate is administered as a pharmaceutical composition comprising a pharmaceutically acceptable vehicle and a therapeutically effective amount of the (2R)-2-phenylcarbonyloxypropyl (2S)-2-amino-3-(3,4-dihydroxyphenyl)propanoate mesylate.

3. The method of claim 2, wherein the pharmaceutical composition is formulated for sustained release oral administration.

4. The method of claim 2, wherein the pharmaceutical composition comprises at least one other diastereomer of 2-phenylcarbonyloxypropyl-2-amino-3-(3,4-dihydroxyphenyl)propanoate mesylate wherein the diastereomeric purity of the (2R)-2-phenylcarbonyloxypropyl (2S)-2-amino-3-(3,4-dihydroxyphenyl)propanoate mesylate is at least 90%.

5. The method of claim 2, wherein the pharmaceutical composition comprises an L-aromatic amino acid decarboxylase inhibitor.

6. The method of claim 2, wherein the pharmaceutical composition comprises a catechol-O-methyltransferase inhibitor.

7. The method of claim 2, wherein the pharmaceutical composition comprises an L-aromatic amino acid decarboxylase inhibitor and a catechol-O-methyltransferase inhibitor.

8. A method of treating a disease selected from depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, and excessive daytime sleepiness in a patient, comprising administering to a patient in need of such treatment a therapeutically effective amount of (2R)-2-phenylcarbonyloxypropyl (2S)-2-amino-3-(3,4-dihydroxyphenyl)propanoate mesylate.

9. The method of claim 8, wherein the (2R)-2-phenylcarbonyloxypropyl (2S)-2-amino-3-(3,4-dihydroxyphenyl)propanoate mesylate is administered as a pharmaceutical composition comprising a pharmaceutically acceptable vehicle and a therapeutically effective amount of the (2R)-2-phenylcarbonyloxypropyl (2S)-2-amino-3-(3,4-dihydroxyphenyl) propanoate mesylate.

10. The method of claim 9, wherein the pharmaceutical composition is formulated for sustained release oral administration.

11. The method of claim 9, wherein the pharmaceutical composition comprises at least one other diastereomer of 2-phenylcarbonyloxypropyl-2-amino-3-(3,4-dihydroxyphenyl)propanoate mesylate wherein the diastereomeric purity of the (2R)-2-phenylcarbonyloxypropyl (2S)-2-amino-3-(3,4-dihydroxyphenyl)propanoate mesylate is at least 90%.

12. The method of claim 9, wherein the pharmaceutical composition comprises an L-aromatic amino acid decarboxylase inhibitor.

13. The method of claim 9, wherein the pharmaceutical composition comprises a catechol-O-methyltransferase inhibitor.

14. The method of claim 9, wherein the pharmaceutical composition comprises an L-aromatic amino acid decarboxylase inhibitor and a catechol-O-methyltransferase inhibitor.

* * * * *